(12) United States Patent
Reinhardt et al.

(10) Patent No.: US 7,303,725 B2
(45) Date of Patent: Dec. 4, 2007

(54) AUTOMATED HIGH VOLUME SLIDE STAINING SYSTEM

(75) Inventors: Kurt Reinhardt, Tucson, AZ (US); Charles D. Lemme, Tucson, AZ (US); Glen Ward, Tucson, AZ (US); William Richards, Tucson, AZ (US); Wayne Showalter, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 704 days.

(21) Appl. No.: 10/414,804

(22) Filed: Apr. 15, 2003

(65) Prior Publication Data

US 2004/0002163 A1 Jan. 1, 2004

Related U.S. Application Data

(60) Provisional application No. 60/372,506, filed on Apr. 15, 2002.

(51) Int. Cl.
*G01N 1/28* (2006.01)
*G01N 1/36* (2006.01)
*G01N 35/00* (2006.01)

(52) U.S. Cl. .............................. 422/63; 422/65; 422/66; 422/67; 422/68.1; 422/64; 436/46; 436/174

(58) Field of Classification Search ................ 422/100, 422/63–67, 68.1; 436/174, 43, 46
See application file for complete search history.

(56) References Cited

U.S. PATENT DOCUMENTS

| | | |
|---|---|---|
| 3,219,416 A | 11/1965 | Natelson |
| 3,574,064 A | 4/1971 | Binnings et al. |
| 3,650,437 A | 3/1972 | Binnings et al. ............. 222/136 |
| 3,665,148 A | 5/1972 | Yasenchak et al. ......... 219/125 |
| 3,695,281 A | 10/1972 | Leon ............................. 137/1 |
| 3,853,092 A | 12/1974 | Amos et al. ................. 118/56 |
| 3,854,703 A | 12/1974 | Gibbs et al. ................. 259/11 |
| 3,979,576 A | 9/1976 | Janson ........................ 219/489 |
| 4,013,038 A | 3/1977 | Rogers et al. ................. 118/5 |
| 4,043,292 A | 8/1977 | Rogers et al. ................. 118/5 |
| 4,058,367 A | 11/1977 | Gilford ........................ 23/253 |
| 4,092,952 A | 6/1978 | Wilkie et al. ................. 118/58 |
| 4,245,967 A | 1/1981 | Busselet ..................... 417/510 |
| RE30,730 E | 9/1981 | Duff ............................ 422/64 |
| 4,286,637 A | 9/1981 | Wilson ........................ 141/374 |
| 4,298,571 A | 11/1981 | DiFulvio et al. ............. 422/65 |
| 4,346,056 A | 8/1982 | Sakurada ..................... 422/64 |
| 4,358,470 A | 11/1982 | Rasmussen ................... 427/4 |

(Continued)

FOREIGN PATENT DOCUMENTS

EP 0 240 134 2/1987

(Continued)

OTHER PUBLICATIONS

"Capillary Action Slide Stainers for Histology and Cytology" Article from Fisher Scientific, 4 pgs.

(Continued)

*Primary Examiner*—Brian R. Gordon

(57) ABSTRACT

An automated slide processing apparatus includes a plurality of work stations arranged in a stack, and a transport/elevator for transporting slides between the various work stations.

33 Claims, 17 Drawing Sheets

U.S. PATENT DOCUMENTS

| | | | | |
|---|---|---|---|---|
| 4,384,193 A | 5/1983 | Kledzik et al. | | 219/521 |
| 4,406,547 A | 9/1983 | Aihara | | 356/414 |
| 4,430,299 A | 2/1984 | Horne | | 422/64 |
| 4,447,395 A | 5/1984 | Englar et al. | | 422/68 |
| 4,455,280 A | 6/1984 | Shinohara et al. | | 422/63 |
| 4,484,293 A | 11/1984 | Minucciani et al. | | 364/513 |
| 4,528,159 A | 7/1985 | Liston | | 422/65 |
| 4,539,855 A | 9/1985 | Jacobs | | 73/864 |
| 4,543,236 A | 9/1985 | von Gise | | 422/50 |
| 4,577,514 A | 3/1986 | Bradley et al. | | 73/863.01 |
| 4,584,275 A | * 4/1986 | Okano et al. | | 435/287.3 |
| 4,629,862 A | 12/1986 | Kitagawa et al. | | 219/200 |
| 4,643,879 A | 2/1987 | Hanaway | | |
| 4,647,431 A | 3/1987 | Sekine et al. | | 422/63 |
| 4,648,023 A | 3/1987 | Powell | | 364/156 |
| 4,659,971 A | 4/1987 | Suzuki et al. | | 318/568 |
| 4,670,974 A | 6/1987 | Antoszewski et al. | | 29/701 |
| 4,676,951 A | * 6/1987 | Armes et al. | | 422/65 |
| 4,678,752 A | 7/1987 | Thorne et al. | | 435/291 |
| 4,681,741 A | 7/1987 | Hanaway | | 422/100 |
| 4,695,430 A | 9/1987 | Coville et al. | | 422/65 |
| 4,708,886 A | 11/1987 | Nelson | | 422/72 |
| 4,720,463 A | * 1/1988 | Farber et al. | | 435/286.5 |
| 4,727,409 A | 2/1988 | Conner et al. | | 357/59 |
| 4,727,494 A | 2/1988 | Buote | | 364/513 |
| 4,729,661 A | 3/1988 | Bell | | 356/437 |
| 4,731,335 A | 3/1988 | Brigati | | 436/180 |
| 4,738,824 A | 4/1988 | Takeuchi | | 422/63 |
| 4,764,342 A | 8/1988 | Kelln et al. | | 422/72 |
| 4,774,055 A | 9/1988 | Wakatake et al. | | 422/64 |
| 4,777,020 A | 10/1988 | Brigati | | 422/99 |
| 4,781,891 A | 11/1988 | Galle et al. | | 422/64 |
| 4,795,710 A | 1/1989 | Muszak et al. | | 435/287 |
| 4,798,706 A | 1/1989 | Brigati | | 422/102 |
| 4,801,431 A | 1/1989 | Cuomo et al. | | 422/104 |
| 4,805,469 A | 2/1989 | Commarmot | | 73/864.81 |
| 4,807,152 A | 2/1989 | Lane et al. | | 364/513 |
| 4,815,978 A | 3/1989 | Mazza et al. | | 435/4 |
| 4,835,711 A | 5/1989 | Hutchins et al. | | 364/513 |
| 4,837,159 A | 6/1989 | Yamada | | 436/45 |
| 4,843,566 A | 6/1989 | Gordon et al. | | 364/513 |
| 4,844,868 A | 7/1989 | Rokugawa | | 422/64 |
| 4,847,208 A | 7/1989 | Bogen | | 436/174 |
| 4,852,001 A | 7/1989 | Tsushima et al. | | 364/401 |
| 4,855,109 A | 8/1989 | Muraishi et al. | | 422/63 |
| 4,857,272 A | * 8/1989 | Sugaya | | 422/65 |
| 4,858,155 A | 8/1989 | Okawa et al. | | 364/557 |
| 4,865,986 A | 9/1989 | Coy et al. | | 435/290 |
| 4,895,706 A | 1/1990 | Root et al. | | 422/102 |
| 4,896,269 A | 1/1990 | Tong | | 364/468 |
| 4,902,481 A | 2/1990 | Clark et al. | | 422/101 |
| 4,911,098 A | 3/1990 | Tabata | | 118/423 |
| 4,919,887 A | 4/1990 | Wakatake | | 422/67 |
| 4,928,540 A | * 5/1990 | Kido et al. | | 73/864.11 |
| 4,933,146 A | 6/1990 | Meyer et al. | | 422/63 |
| 4,935,875 A | 6/1990 | Shah et al. | | 364/497 |
| 4,961,906 A | 10/1990 | Andersen et al. | | 422/102 |
| 4,964,544 A | 10/1990 | Hanna et al. | | 222/181 |
| 4,965,049 A | 10/1990 | Lillig et al. | | 422/68.1 |
| 4,971,913 A | 11/1990 | Manabe et al. | | 436/55 |
| 4,975,250 A | 12/1990 | Mordecki | | 422/99 |
| 4,979,093 A | 12/1990 | Laine et al. | | 364/167.01 |
| 4,979,128 A | 12/1990 | Seki et al. | | 364/513 |
| 4,985,206 A | 1/1991 | Bowman et al. | | 422/99 |
| 5,002,736 A | 3/1991 | Babbitt et al. | | 422/100 |
| 5,023,187 A | 6/1991 | Koebler et al. | | 436/180 |
| 5,035,866 A | 7/1991 | Wannlund | | 422/102 |
| 5,040,123 A | 8/1991 | Barber et al. | | 364/468 |
| 5,051,238 A | 9/1991 | Umetsu et al. | | 422/64 |
| 5,073,504 A | 12/1991 | Bogen | | 436/174 |
| 5,075,079 A | 12/1991 | Kerr et al. | | 422/64 |
| 5,089,229 A | 2/1992 | Heidt et al. | | 422/64 |
| 5,093,557 A | 3/1992 | Lok et al. | | 219/388 |
| 5,096,670 A | 3/1992 | Harris et al. | | 422/65 |
| 5,104,621 A | 4/1992 | Pfost et al. | | |
| 5,105,066 A | 4/1992 | Houdy et al. | | 219/385 |
| 5,116,496 A | 5/1992 | Scott | | 210/232 |
| 5,122,342 A | 6/1992 | McCulloch et al. | | 422/65 |
| 5,122,959 A | 6/1992 | Nathanson et al. | | 364/436 |
| 5,148,370 A | 9/1992 | Litt et al. | | 364/468 |
| 5,154,889 A | 10/1992 | Muraishi | | 422/65 |
| 5,168,453 A | 12/1992 | Nomaru et al. | | 364/468 |
| 5,180,606 A | 1/1993 | Stokes et al. | | 427/2 |
| 5,181,259 A | 1/1993 | Rorvig | | 382/36 |
| 5,207,987 A | 5/1993 | Kureshy et al. | | 422/67 |
| 5,209,903 A | 5/1993 | Kanamori et al. | | |
| 5,218,645 A | 6/1993 | Bacus | | 382/6 |
| 5,229,074 A | 7/1993 | Heath et al. | | 422/64 |
| 5,231,029 A | 7/1993 | Wootton et al. | | 435/289 |
| 5,232,664 A | 8/1993 | Krawzak et al. | | 422/64 |
| 5,232,665 A | * 8/1993 | Burkovich et al. | | 422/65 |
| 5,233,533 A | 8/1993 | Edstrom et al. | | 364/468 |
| 5,246,665 A | 9/1993 | Tyranski et al. | | 422/64 |
| 5,266,272 A | 11/1993 | Griner et al. | | |
| 5,273,905 A | 12/1993 | Muller et al. | | 435/301 |
| 5,280,156 A | 1/1994 | Niori et al. | | 219/385 |
| 5,282,149 A | 1/1994 | Grandone et al. | | 364/497 |
| 5,304,347 A | 4/1994 | Mann et al. | | 422/67 |
| 5,311,426 A | 5/1994 | Donohue et al. | | 364/413.09 |
| 5,314,825 A | 5/1994 | Weyrauch et al. | | 436/43 |
| 5,316,452 A | 5/1994 | Bogen et al. | | 417/412 |
| 5,316,726 A | 5/1994 | Babson et al. | | 422/65 |
| 5,332,549 A | * 7/1994 | MacIndoe, Jr. | | 422/63 |
| 5,334,353 A | 8/1994 | Blattner | | 422/100 |
| 5,352,612 A | 10/1994 | Huber et al. | | 436/47 |
| 5,355,439 A | 10/1994 | Bernstein et al. | | 395/82 |
| 5,355,695 A | 10/1994 | Kawaguchi et al. | | 62/498 |
| 5,356,814 A | 10/1994 | Carrico, Jr. et al. | | 435/286 |
| 5,358,691 A | 10/1994 | Clark et al. | | 422/64 |
| 5,376,313 A | 12/1994 | Kanewske, III et al. | | 264/1.1 |
| 5,402,350 A | 3/1995 | Kline | | 364/468 |
| 5,424,036 A | 6/1995 | Ushikubo | | 422/64 |
| 5,425,918 A | 6/1995 | Healey et al. | | 422/64 |
| 5,428,470 A | 6/1995 | Labriola, II | | 359/119 |
| 5,431,309 A | 7/1995 | Ophardt | | 222/181.3 |
| 5,439,645 A | 8/1995 | Saralegui et al. | | 422/64 |
| 5,439,649 A | 8/1995 | Tseung et al. | | 422/99 |
| 5,446,652 A | 8/1995 | Peterson et al. | | 364/578 |
| 5,475,610 A | 12/1995 | Atwood et al. | | 364/500 |
| 5,479,581 A | 12/1995 | Kleinschnitz | | 395/82 |
| 5,496,518 A | 3/1996 | Arai et al. | | 422/64 |
| 5,512,248 A | 4/1996 | Van | | 422/100 |
| 5,523,056 A | 6/1996 | Miller | | 422/64 |
| 5,525,302 A | 6/1996 | Astle | | 422/100 |
| 5,525,515 A | 6/1996 | Blattner | | 436/49 |
| 5,573,727 A | 11/1996 | Keefe | | 422/63 |
| 5,575,976 A | 11/1996 | Choperena et al. | | 422/64 |
| 5,576,215 A | 11/1996 | Burns et al. | | 436/50 |
| 5,578,455 A | 11/1996 | Tosa et al. | | 435/7.32 |
| 5,595,707 A | 1/1997 | Copeland et al. | | 422/64 |
| 5,601,141 A | 2/1997 | Gordon et al. | | 165/263 |
| 5,629,201 A | 5/1997 | Nugteren et al. | | 435/283.1 |
| 5,639,665 A | 6/1997 | Arai et al. | | 436/50 |
| 5,645,114 A | 7/1997 | Bogen et al. | | 141/145 |
| 5,645,800 A | * 7/1997 | Masterson et al. | | 422/65 |
| 5,646,046 A | 7/1997 | Fischer et al. | | 436/49 |
| 5,646,049 A | 7/1997 | Tayi | | 436/518 |
| 5,650,327 A | 7/1997 | Copeland et al. | | 436/46 |
| 5,654,199 A | 8/1997 | Copeland et al. | | 436/46 |
| 5,654,200 A | 8/1997 | Copeland et al. | | 436/46 |
| 5,656,493 A | 8/1997 | Mullis et al. | | 435/286.1 |
| 5,672,512 A | * 9/1997 | Shaw | | 436/6 |
| 5,674,454 A | * 10/1997 | Karl et al. | | 422/63 |
| 5,675,715 A | 10/1997 | Bernstein et al. | | 395/82 |

| | | | |
|---|---|---|---|
| 5,695,718 A | 12/1997 | Imai et al. ............. 422/62 |
| 5,696,887 A | 12/1997 | Bernstein et al. ............. 395/82 |
| 5,700,346 A | 12/1997 | Edwards ............. 156/357 |
| 5,736,105 A | 4/1998 | Astle ............. 422/100 |
| 5,737,498 A | 4/1998 | Murray ............. 395/81 |
| 5,737,499 A | 4/1998 | Bernstein et al. ............. 395/82 |
| 5,819,842 A | 10/1998 | Potter et al. ............. 165/206 |
| 5,839,091 A | 11/1998 | Rhett et al. ............. 702/19 |
| 5,854,075 A * | 12/1998 | Levine et al. ............. 436/46 |
| 5,861,094 A | 1/1999 | Gochde ............. 210/232 |
| 5,871,696 A * | 2/1999 | Roberts et al. ............. 422/65 |
| 5,875,286 A | 2/1999 | Bernstein et al. ............. 395/82 |
| 5,895,628 A | 4/1999 | Heid et al. ............. 422/65 |
| 5,909,674 A | 6/1999 | Schaffer et al. ............. 706/13 |
| 5,930,461 A | 7/1999 | Bernstein et al. ............. 395/82 |
| 5,947,167 A | 9/1999 | Bogen et al. ............. 141/1 |
| 5,948,359 A * | 9/1999 | Kalra et al. ............. 422/65 |
| 5,958,341 A | 9/1999 | Chu |
| 5,975,740 A | 11/1999 | Lin et al. ............. 364/468.05 |
| 5,985,669 A | 11/1999 | Palander |
| 5,985,672 A | 11/1999 | Kegelman et al. ............. 436/50 |
| 6,004,512 A * | 12/1999 | Titcomb et al. ............. 422/63 |
| 6,017,495 A | 1/2000 | Ljungmann ............. 422/65 |
| 6,054,099 A | 4/2000 | Levy ............. 422/102 |
| 6,068,393 A | 5/2000 | Hutchins et al. ......... 364/468.19 |
| 6,076,583 A | 6/2000 | Edwards ............. 156/539 |
| 6,080,363 A | 6/2000 | Takahashi et al. |
| 6,093,574 A | 7/2000 | Druyor-Sancehs et al. . 436/180 |
| 6,096,271 A | 8/2000 | Bogen et al. ............. 422/64 |
| 6,180,060 B1 | 1/2001 | Green et al. ............. 422/64 |
| 6,180,061 B1 | 1/2001 | Bogen et al. |
| 6,183,645 B1 | 2/2001 | DeWitt ............. 210/634 |
| 6,183,693 B1 | 2/2001 | Bogen et al. ............. 422/64 |
| 6,193,933 B1 | 2/2001 | Sasaki et al. ............. 422/64 |
| 6,296,764 B1 | 10/2001 | Guirguis et al. ......... 210/323.1 |
| 6,296,809 B1 | 10/2001 | Richards et al. ............. 422/64 |
| 6,349,264 B1 | 2/2002 | Rhett et al. ............. 702/19 |
| 6,352,861 B1 | 3/2002 | Copeland et al. ............. 436/46 |
| 6,368,067 B1 | 4/2002 | Stutz |
| 6,372,144 B1 | 4/2002 | Vassarotti ............. 210/650 |
| 6,387,326 B1 | 5/2002 | Edwards et al. ............. 422/63 |
| 6,395,554 B1* | 5/2002 | Regan et al. ............. 436/46 |
| 6,436,348 B1 | 8/2002 | Ljungmann et al. ............. 422/63 |
| 6,451,551 B1 | 9/2002 | Zhan et al. |
| 6,471,958 B2 | 10/2002 | Dimitrijevich et al. .... 424/93.7 |
| 6,495,106 B1 | 12/2002 | Kalra et al. |
| 6,537,818 B2 | 3/2003 | Reinhardt et al. ............. 436/54 |
| 6,594,537 B1 | 7/2003 | Bernstein et al. ............. 700/100 |
| 6,632,598 B1 | 10/2003 | Zhang et al. |
| 6,635,225 B1* | 10/2003 | Thiem et al. ............. 422/65 |
| 6,649,128 B1* | 11/2003 | Meyer et al. ............. 422/65 |
| 6,685,884 B2* | 2/2004 | Stylli et al. ............. 422/63 |
| 6,703,247 B1* | 3/2004 | Chu ............. 436/180 |
| 6,746,851 B1 | 6/2004 | Tseung et al. |
| 6,881,579 B2* | 4/2005 | Hilson et al. ............. 436/47 |
| 6,887,428 B2* | 5/2005 | Wernz et al. ............. 422/63 |
| 6,998,094 B2* | 2/2006 | Haslam et al. ............. 422/65 |
| 2001/0004449 A1 | 6/2001 | Suzuki et al. ............. 422/100 |
| 2001/0016358 A1 | 8/2001 | Osawa et al. ............. 436/180 |
| 2001/0019703 A1 | 9/2001 | Thiem et al. |
| 2001/0055545 A1 | 12/2001 | Takii et al. ............. 422/100 |
| 2002/0037239 A1 | 3/2002 | Komatsu ............. 422/100 |
| 2002/0054830 A1* | 5/2002 | Bogen et al. ............. 422/64 |
| 2002/0057992 A1 | 5/2002 | Eckert et al. ............. 422/63 |
| 2002/0064482 A1* | 5/2002 | Tisone et al. ............. 422/100 |
| 2002/0116132 A1 | 8/2002 | Rhett et al. ............. 702/19 |
| 2003/0026732 A1* | 2/2003 | Gordon et al. ............. 422/63 |
| 2003/0047863 A1 | 3/2003 | Lang et al. |
| 2003/0092186 A1* | 5/2003 | Pressman et al. ............. 436/46 |
| 2003/0099580 A1* | 5/2003 | Pressman et al. ............. 422/104 |
| 2003/0203493 A1* | 10/2003 | Lemme et al. ............. 436/46 |
| 2003/0215357 A1* | 11/2003 | Malterer et al. ............. 422/50 |
| 2004/0002163 A1 | 1/2004 | Reinhardt et al. |
| 2004/0038408 A1* | 2/2004 | Abbott et al. ............. 436/4 |
| 2004/0052685 A1 | 3/2004 | Richards et al. |
| 2004/0092024 A1 | 5/2004 | Reinhardt et al. |
| 2004/0121485 A1 | 6/2004 | Hopkins et al. |
| 2005/0042137 A1* | 2/2005 | Petersen et al. ............. 422/58 |
| 2005/0047971 A1* | 3/2005 | Clements et al. ............. 422/102 |
| 2005/0053526 A1* | 3/2005 | Angros ............. 422/100 |
| 2005/0186114 A1* | 8/2005 | Reinhardt et al. ............. 422/65 |

FOREIGN PATENT DOCUMENTS

| | | |
|---|---|---|
| EP | 0517835 | 2/1996 |
| EP | 0722363 | 4/1999 |
| EP | 0600939 | 10/1999 |
| EP | 1 052 497 A2 | 11/2000 |
| EP | 1 052 497 A3 | 1/2003 |
| EP | 1477838 A2 | 11/2004 |
| FR | 2 239 167 | 1/1967 |
| FR | 2 528 122 | 4/1982 |
| GB | 2143205 | 2/1985 |
| GB | 2 216 259 | 10/1989 |
| JP | 55-107957 | 2/1979 |
| JP | 55-014157 | 3/1980 |
| JP | 63-208761 | 8/1988 |
| JP | 04-356845 | 12/1992 |
| WO | WO 87/00086 | 1/1987 |
| WO | WO 88/02865 | 4/1988 |
| WO | WO 91/13335 | 9/1991 |
| WO | WO 92/01919 | 2/1992 |
| WO | WO 93/23732 | 11/1993 |
| WO | PCT/US98/16604 | 12/1998 |
| WO | WO 00/14534 | 3/2000 |
| WO | WO 00/62035 | 10/2000 |
| WO | WO 01/51909 | 7/2001 |
| WO | WO 01/73399 | 10/2001 |
| WO | WO 03/045560 | 6/2003 |
| WO | WO 03/052386 | 6/2003 |

OTHER PUBLICATIONS

"The New Protocol in Staining Technology" Article from Fisher HealthCare, 5 pgs.
"Sakura Tisse-Tek DRS 2000 Slide Stainer" article from Sakura Finetek U.S.A., Inc., 1998, 1 pg.
"Tissue-Tek DRS 2000 Slide Stainer, Computer-Assisted Flexibility for Unmatched Productivity" Article from Sakura Finetek U.S.A., Inc., 1998, 4 pgs.
"Tissue-Tek DRS 2000 Automatic Multiple Slide Stainer, Multiple with Double Quality" Article from Sakura FinetekEurope B.V., 1998, 4 pgs.
"Coverslippers & Stainers" Article off of www.backerinstruments.com.
"Varistain XY Multi-Program Robotic Slide Stainer" Article from Shandon, Inc., 1991, 8 pgs.
"Varistain 24-4 Flexible, Efficient Automatic Slide Stainer" Article from Shandon, Inc., 1991, 8 pgs.
"Varistain 24-4 K High Throughput Continuous Slide Stainer" Article from Shandon, Inc., 2 pgs.
"Laboratory Equipment 1998 And 1999" Article from Shandon, pp. 37-51.
"Staining" p. 17.
"Advanta CV/AS" Article from Vision Instruments, 2 pgs.
"Leica Autostainer XL" Article from Leica, 4 pgs.
"Tissue-Stainer TST 40 " Article from Medite, 2 pgs.
"A Versatile and Functional Family fo Tissue Staining Products. TST Stainer Trio" Article from Mopec, 7 pgs.
"Robot-Stainer HMS 760, Automatic Slide Stainer for Routine Histology and Cytology Applications" Article from Microm Histology Products, 4 pgs.
"All In One-All At Once" Article from BioGenex, 4 pgs.
Conference proceedings presented ant the 2000 National Society for Histotechnology Convention, from BioGenex, 2 pgs.
"DAKO Autostainer Features & Specifications" Article from www.dakousa.com, 3 pgs.

"ST 5050 Zymed's Sensible IHC Automated Staining Solution" Article from Zymed Laboratories, 2 pgs.

"II Analytical Systems, Discrete Automated Chemistry System with Tableted Reagents" Driscoll et al., Clin. Chem. 29/9, 1983, pp. 1609-1615.

"Concurrent HPLC Analyses of Carbohydrate Distribution and 5-(Hydroxymethyl)-2-Furaldehyde Usign Robotics" Mueller et al., Journal of Chromatographic Science, vol. 25, 1987, pp. 198-201.

"Robotics for the Bioanalytical Laboratory-A Flexible System for the Analysis of Drugs in Biological Fluids" Fouda et al., Trac Trends in Analytical Chemistry, 10 pgs.

"The SimKit Sytem: Knowledge-Based Simulation and Modeling Tools in KEE" Stelzner et al., An Intellicorp Technical Article, 1987, 22 pgs.

"Anatomic Viral Detection Is Automated: The Application of a Robotic Molecular Pathology System for the Detection of DNA Viruses in Anatomic Pathology Substrates, Using Immunocytochemical and Nucleic Acid Hybridization Techniques" Montone et al., The Yale Journal of Biology and Medicine, 62, 1989, pp. 141-158.

"Viral Diagnosis by in situ Hybridization, Description of a Rapid Simplified Colorimetric Method" Unger et al., The American Journal of Surgical Pathology, 10(1), 1986, pp. 1-8.

"Colorimetric In-Situ Hybridization in Clinical Virology: Development of Automated Technology" Unger et al., Current Topics in Microbiology and Immunology, vol. 143, 1989, pp. 21-31.

"Laboratory Robotics and Arificial Intelligence" Isenhour et al., Clinical Chemistry, 36/9, 1990, pp. 1561-1566.

"Intelligent Robots-The Next Step in Laboratory Automation" Isenhour et al., Analytical Chemistry, vol. 61, No. 13, 1989, pp. 805-814.

"TORTS: An Expert System for Temporal Optimization of Robotic Procedures" Isenhour et al., Journal of Chemical Information and Computer Sciences, No. 28, 1988, pp. 215-221.

"Robotics in the Laboratory" Isenhour, Journal of Chemical Information and Computer Sciences, No. 25, 1985, pp. 292-295.

"Robot Task Planning System Based on Product Modeling" Kawaba et al., pp. 471-476.

"Robotic Work Station for Microscale Synthetic Chemistry: On-Line Absorptior Spectroscopy, Quantitative Automated Thin-Layer Chromatography, and Multiple Reactions in Parallel" Lindsey et al., Rev. Sci. Instrum., 59(6), 1988, pp. 940-950.

"Job Sequencing with Fuzzy Processing Times" McCahon et al., An International Journal Computers & Mathematics with Applications, vol. 19, No. 7, 1990, pp. 31-41.

"Scheduling Project Networks with Resource Constraints and Time Windows" Bartusch et al., Annals of Operations Research, 16, 1988, pp. 201-140.

"Basic Structure of Computers" Hamacher et al., Computer Organization Second Edition, pp. 1-14.

"A Guide to GUIs" Hayes et al., Byte, 1989, pp. 250-257.

"Robot Simulator in Tips/Geometric Simulator" Okino et al., Robotics and Computer Integrated Manufacturing, vol. 3, No. 4, 1987, pp. 429-437.

"Robot Task Planning: Programming Using Interactive Computer Graphics" Sjolund et al, pp. 7-122-7-135.

"Time Window Constrained Routing and Scheduling Problems" Solomon et al., Transportaion Science, vol. 22, No. 1, 1988, pp. 1-13.

"The Abbott IMx Automated Benchtop Immunochemistry Analyzer System" Flore et al., Clin. Chem. 34/9, 1988, pp. 1726-1732.

"Early Development of the Modern Robot" Critchlow, Introduction to Robotics, Chapter 2, pp. 37-56, Chapter 6, pp. 151-213.

"An Automated Device for immunocytochemistry" Stark et al., Journal of Innumological Methods, 107, 1988, pp. 89-92.

"Automated Immunochemistry" MaWhinney et al., Journal Clin Pathol. 1990, pp. 591-596.

"Automation of APAAP Immunocytochemical Technique" Stross et al., Journal Clin. Pathol., No. 42, 1989, pp. 106-112.

Mewburn Ellis letter to EPO including revised set of claims for EPO Appl. No. 91906210.9.

German List "Anlage K5" Merkmalsgliederung Anspruch 1.

"DNA Sequencing with Thermus Aquaticus DNA Polymerase and Direct Sequencing of Polymerase Chain Reaction-Amplified DNA" Innis et al., Proc. Natl. Acad. Sci. USA , No. 85, 1988, pp. 9436-9440.

"Enzymatic Amplification of B-Globin Genomic Sequences and Restriction Site Analysis for Diagnosis of Sickle Cell Anemia" Saiki et al., Science vol. 230, 1985, pp. 1350-1354.

File History of 488601 in German, 2 pgs.

* cited by examiner

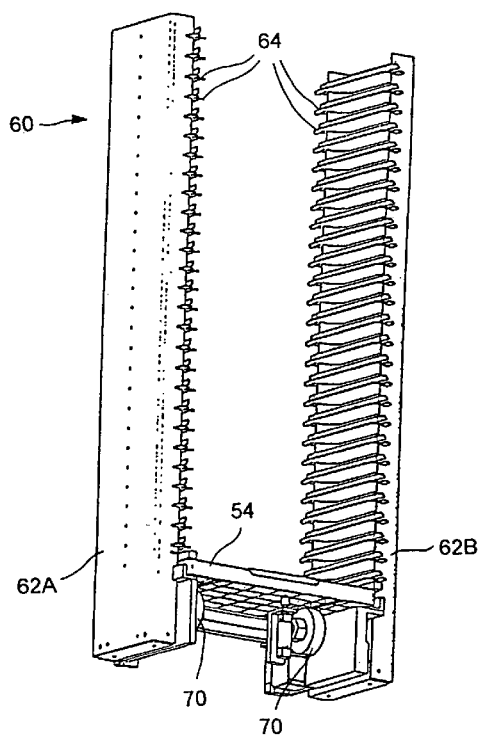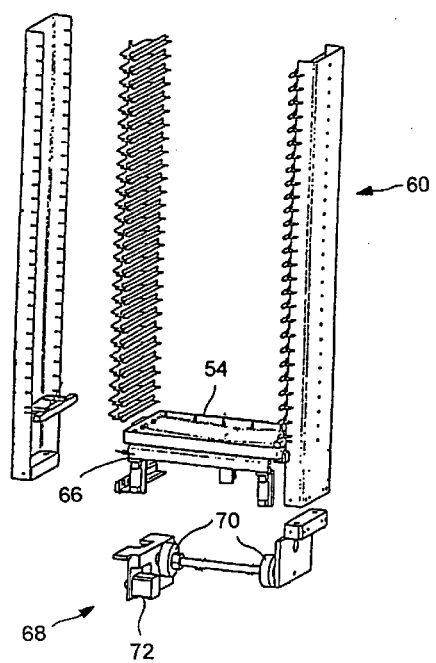
FIG. 1C
FIG. 1D

AUTOMATED HIGH VOLUME SLIDE STAINING SYSTEM

CROSS-REFERENCE TO RELATED APPLICATIONS

This Application claims benefit of U.S. Provisional Application Ser. No. 60/372,506, filed Apr. 15, 2002.

FIELD OF THE INVENTION

The present invention relates to medical diagnostic equipment. The invention has particular utility in connection with the automated staining of biological samples on microscope slides, and will be described in connection with such utility, although other utilities are contemplated.

BACKGROUND OF THE INVENTION

Many tissues do not retain enough color after processing to make their components visible under a bright-field microscope. Accordingly, it is a common practice to add color or dies to tissues by staining them. The hematoxylin and eosin ("H&E") stain is probably the most widely used histological stain. Its popularity is based on its comparative simplicity and ability to demonstrate clearly an enormous number of different tissue structures. Hematoxylin can be prepared in numerous ways and has a widespread applicability to tissues from different sites. Essentially, the hematoxylin component stains the cell nuclei blue/black, with good intranuclear detail, while the eosin stains cell cytoplasm and most connective tissue fibers in varying shades and intensities of pink, orange and red.

Accurate diagnosis depends on a pathologist or cytologist examining stained microscope slides, usually H&E paraffin sections, the H&E staining having been carried out in bulk by an automated staining machine. The need for consistency is vital to avoid difficult histological interpretation. In general, automated staining machines allow accurate and consistent staining, differentiation and dehydration by adjusting the times of each step.

Certain standard procedures usually apply to the staining of tissues on the slides. Paraffin sections first must be de-paraffinized, because most stains are applied in either aqueous or alcoholic solutions and will not penetrate paraffin-infiltrated tissues. After the slides are de-paraffinized, the slides typically are baked in an oven or other heated chamber to drive off de-paraffinizing solvent, and adhere the tissues to the slides. The tissues may then be stained using, for example, standard stains such as hematoxylin and eosin. Finally, coverslipping is performed by adhering a thin glass coverslip to the stained tissue section, and then sealing it with a mounting agent, thereby creating a hermetically sealed environment suitable for archiving. Heretofore, all of these steps have been manually performed by a histotechnologist, a vanishing breed of laboratory technician dedicated to the art of preparing and staining of human tissue samples for reading and interpretation by a Pathologist.

There exists a need to automate all of the steps from de-paraffinizing through coverslipping in histotechnology.

SUMMARY OF THE INVENTION

The present invention provides an automated slide-staining system for application of stains to biological tissue sections mounted on microscope slides. More particularly, the present invention provides an automated apparatus for deparaffinizing, staining and coverslipping a plurality of biological specimen bearing slides, in a fully automated and integrated system. In a preferred embodiment, the present invention provides an automated apparatus comprising a plurality of stacked work stations wherein specimen carrying slides may be dried, baked, de-waxed and prepped for staining, stains applied, and the slides sealed or covered so that the slides may then be stored for future analysis and study or as a permanent record of the analysis performed, and a transport elevator for moving a slide tray bearing a plurality of specimen slides between the plurality of work stations. In yet a further embodiment, the invention is directed to a method of automatically preparing tissue samples on microscope slides for pathological analysis, comprising baking the tissue sample onto the slide by having the instrument apply heat to the tissue sufficient to adhere it to the slide; deparaffinizing the tissue sample by contacting it with deparaffinizing fluid at a temperature above the melting point of the paraffin, and subsequently rinsing the liquefied paraffin away; staining the tissue sample by contacting it with a staining reagent; and coverslipping the slide by contacting the stained tissue sample on the slide with a pre-glued coverslip and an adhesive activating fluid.

BRIEF DESCRIPTION OF THE DRAWINGS

Further features and advantages of the present invention will be seen from the following detailed description of the invention, taken in conjunction with the following drawings wherein:

FIG. 1C is a perspective view from the inside, and FIG. 1D a perspective exploded view from the outside of the tray storage station or "garage" portion of the present invention;

DETAILED DESCRIPTION OF FIRST EMBODIMENT

The staining system of the present invention performs all the steps of processing, staining and coverslipping of slide mounted biological samples in an efficient high-speed input operation. More particularly, slides bearing biological samples are placed on a slide tray, and the slide tray bearing the sample slides are loaded into the system in accordance with the present invention wherein the slides are conducted through a sequence of steps in which the slides are baked, de-waxed, stained and finally coverslipped. A method of the present invention is directed to a method of automatically preparing tissue samples on microscope slides for pathological analysis, comprising baking the tissue sample onto the slide by having the instrument apply heat to the tissue sufficient to adhere it to the slide; deparaffinizing the tissue sample by contacting it with deparaffinizing fluid at a temperature above the melting point of the paraffin, and subsequently rinsing the liquefied paraffin away; staining the tissue sample by contacting it with a staining reagent; and coverslipping the slide by contacting the stained tissue sample on the slide with a pre-glued coverslip and an adhesive activating fluid.

Figure 1:
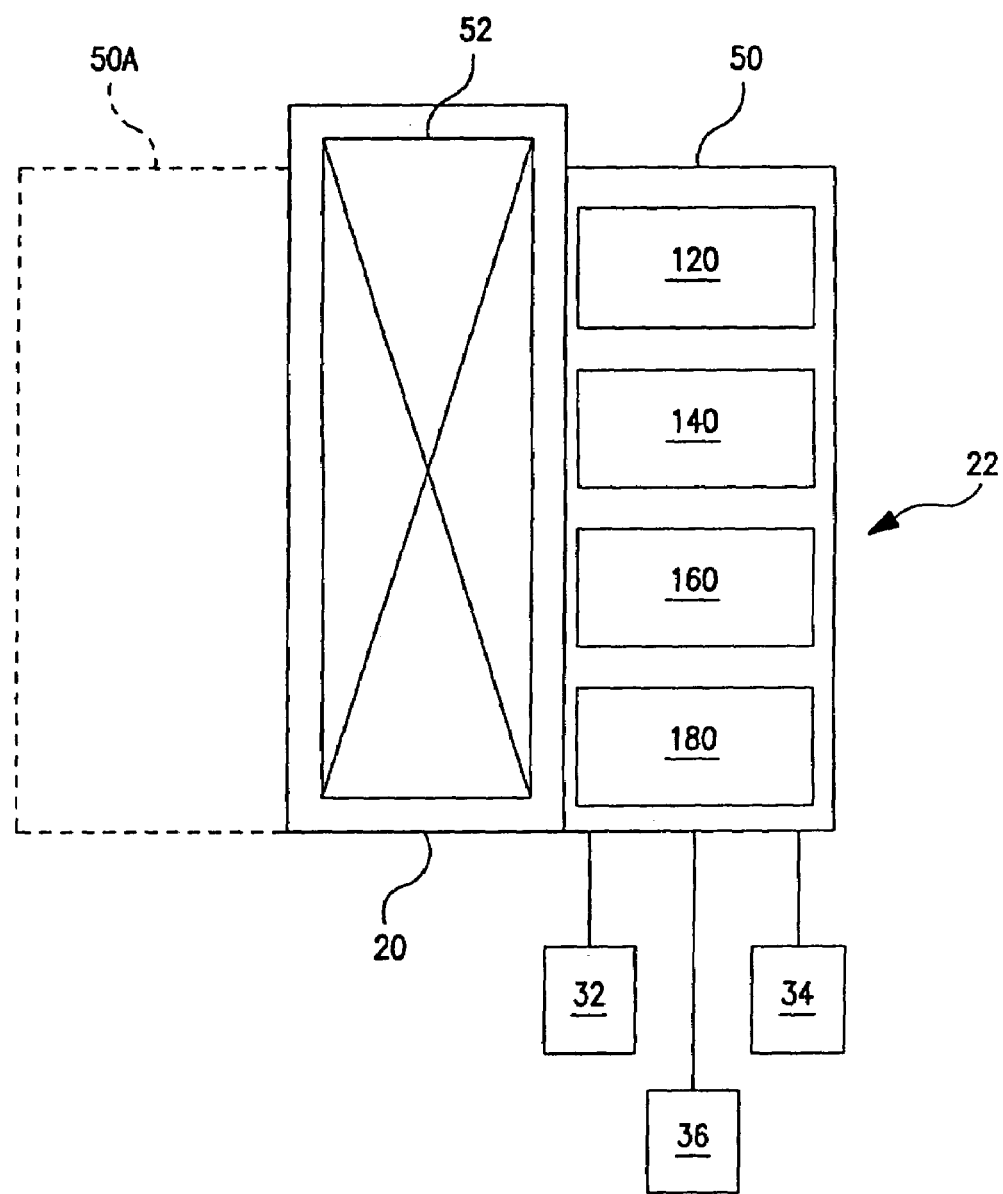
FIG. 1 is a simplified plan view and FIGS. 1A and 1B are fragmentary front and rear perspective views of an automated high-speed staining apparatus made in accordance with a first embodiment of the present invention.

Referring to FIG. 1 of the drawings, the apparatus 20 of the first embodiment of the invention functions as one component or module of a system 22. System 22 also includes bulk fluid containers 32, 34, 36 and related equipment.

Figure 1A:
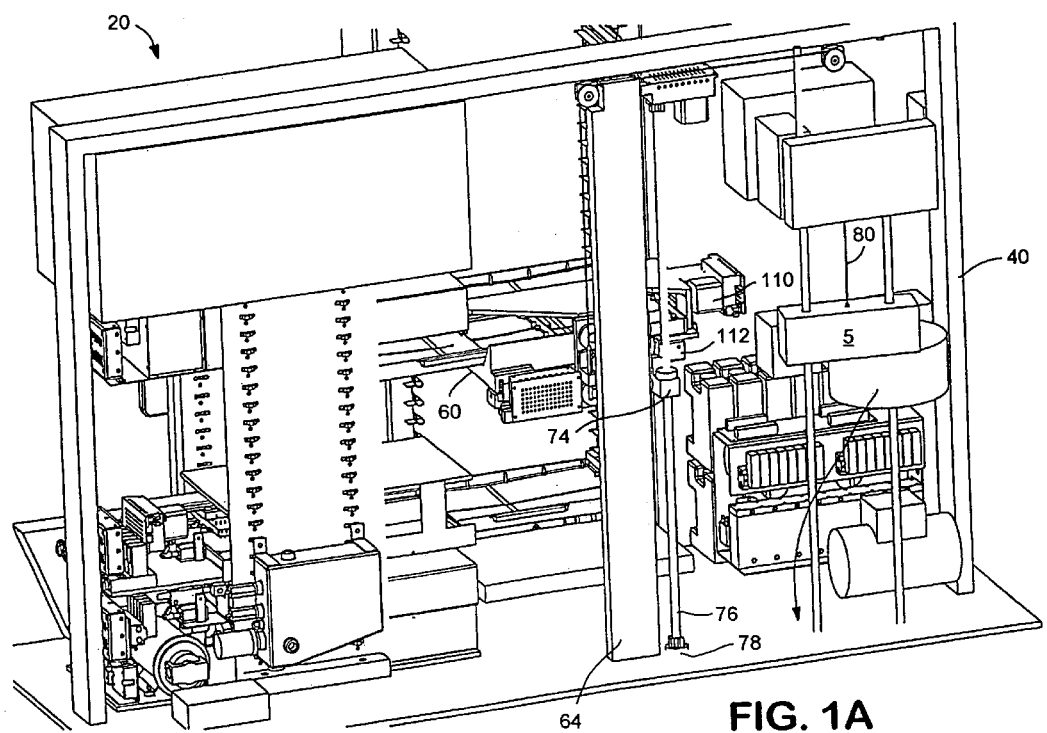
Figure 1B:
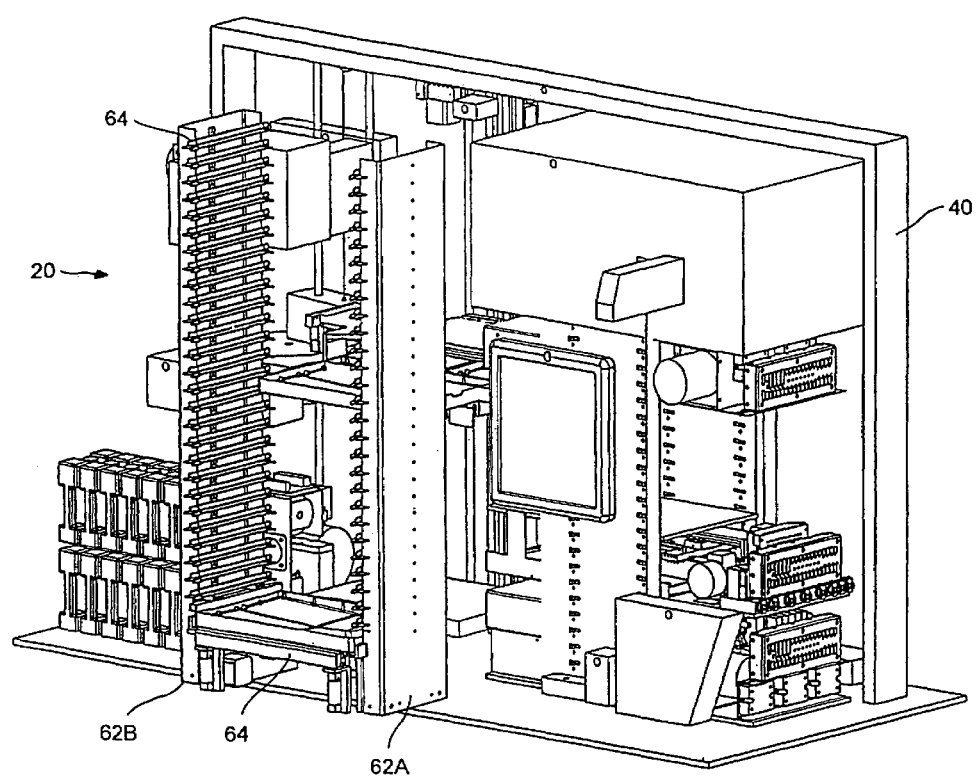

Referring also to FIGS. 1A and 1B, apparatus 20 includes a frame 40 supporting a stack of workstations comprising, for example, one or more drying or baking stations or modules 120, de-waxing or de-paraffinizing station or module 140, one or more staining stations or modules 160 and a coverslipping station or module 180 arranged in a tower 50. A transport and elevator mechanism 52 is provided adjacent tower 50 for transporting a slide tray 54 designed to carry a plurality of individual specimen bearing slides 56 from a tray storage station or "garage" 60 through drying/baking, de-waxing, staining and coverslipping operations.

Referring in particular to FIGS. 1B and 1C, the tray storage garage or station 60 comprises a pair of stanchions 62A, 62B bearing a plurality of vertically spaced shelves or skids 64 for accommodating slide trays 54. Referring also to FIG. 1D, tray storage station or garage 60 includes a pivotally mounted door providing access to a first shelf position (for clarity, the outside skin or cover to garage 60 has been omitted). A tray drive assembly indicated generally at 68 including a pair of rotatably mounted drive wheels 70 driven by a drive motor and transmission 72 is positioned under the first shelf position for moving a tray into and out of the portal 66.

Figure 2:
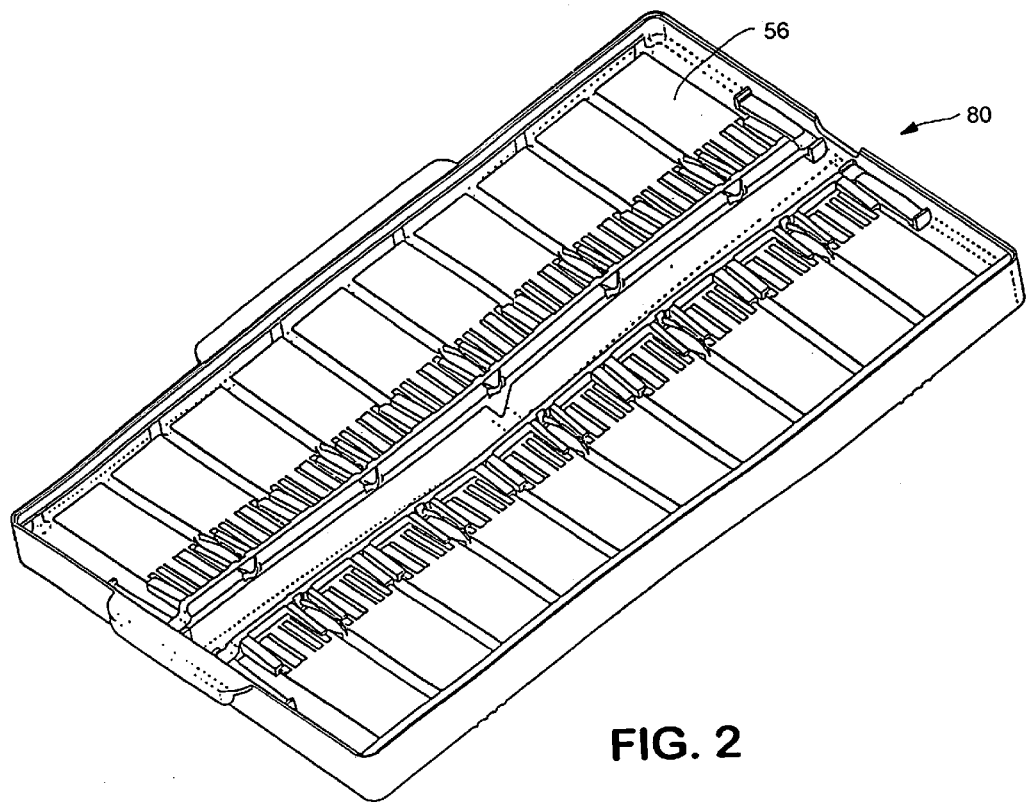
FIG. 2 is a perspective view and FIG. 2A an exploded view showing details of a specimen slide supporting tray employed in the present invention.
Figure 2A:
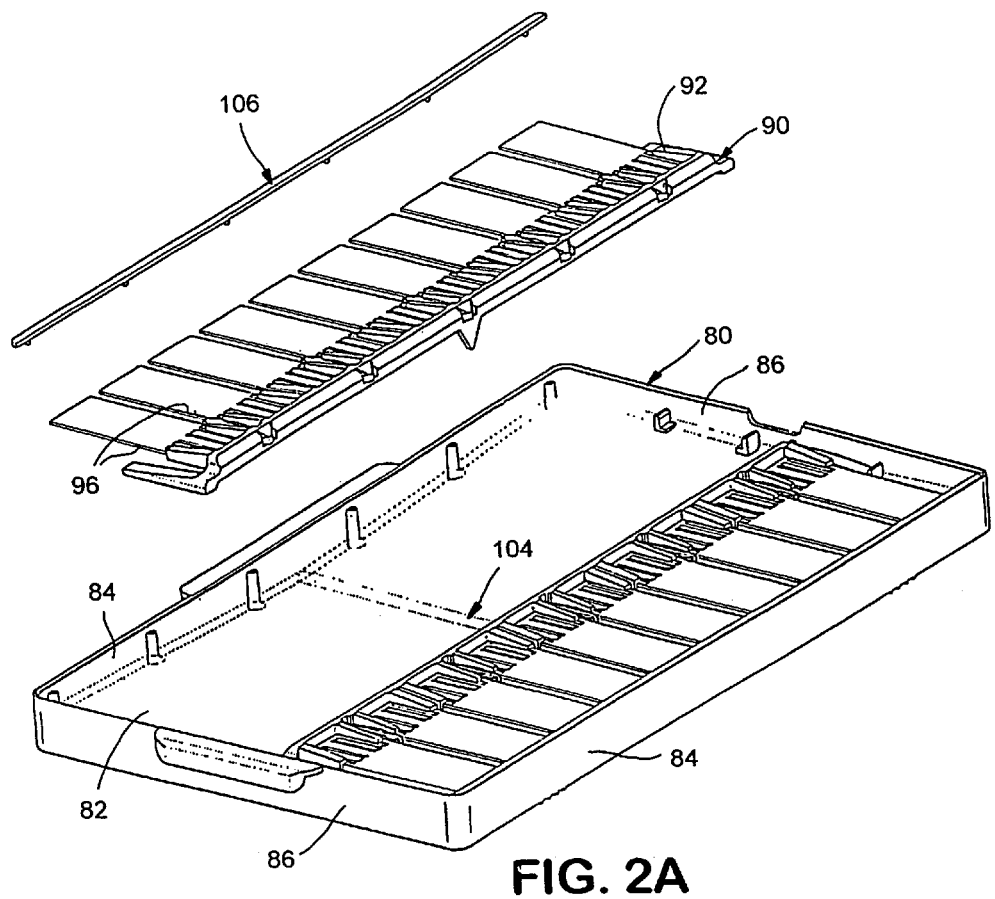

Referring in particular to FIGS. 2 and 2A, the slide tray 54 preferably comprises a pan or slide tray 80 having a generally rectangular plan, including a bottom wall 82, opposed side walls 84 and opposed end walls 86. The slide tray typically is formed by conventional injection molding using synthetic polymers intended for such use, which are well-known in the art.

Tray 80 includes a specimen slide supporting rack 90 for holding specimen slides in a substantially horizontal position in the same plane. Holding all the slides in the same plane facilitates baking and drying, as will be described below, and also prevents cross-contamination of slides during de-paraffinizing and staining as will be described below. Rack 90 includes a plurality of slide spring supports 92 that limit the axial, lateral and vertical movement of specimen slides 56 once placed on the slide tray. Rack 90 is supported above tray bottom 80 at sufficient height to discourage or prevent the formation of films or bubbles forming between the specimen slide bottom and the tray bottom. Slide spring supports 92 hold the individual specimen slides in position by exerting force on opposing edges 96 of the specimen slides. The floor of the slide tray is sloped towards the middle to facilitate drainage to a central location 104 for evacuation of de-waxing fluids and stains, as will be described in detail hereinafter. Tray 80 permits the automated handling of a plurality of specimen slides through of the steps of drying/baking, de-paraffinizing, staining and coverslipping. In a preferred embodiment, tray 80 includes splash rails 106 and is arranged to accommodate 16 specimen slides arranged in a generally horizontal grid two slides wide and eight slides tall.

In the illustrated embodiment, the staining system comprises a drying/baking station or module 120, a de-paraffinizing station or module 140, a staining station or module 160 and a coverslipping station or module 180 vertically arranged in tower 50 and controlled by a computer.

Figure 4:
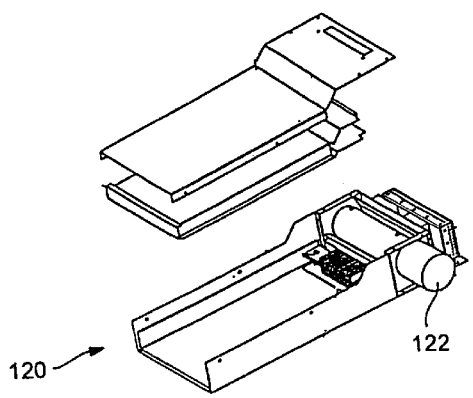
FIG. 4 is a view, similar to FIG. 3, of the heating or baking module of a first embodiment of the present invention.

Referring to FIG. 4, drying/baking station 120 comprises a thermally-insulated compartment into which is supplied controlled heat for drying specimen slides. Drying/baking station 120 preferably comprises a modular unit and includes a convection heater 122, arranged to direct a flow of heated air across the surfaces of the specimen slides. One feature and advantage of the present invention which results from the horizontal presentation of the slides is that convection drying is particularly efficient.

Figure 3A:
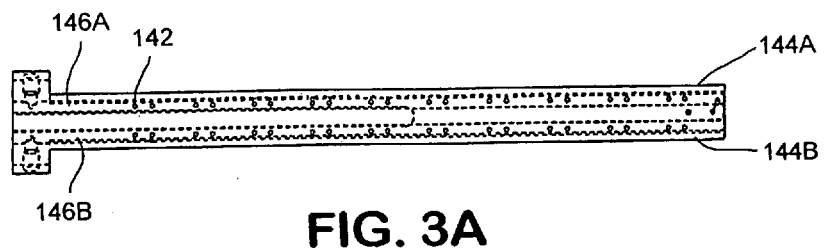
FIG. 3A is a top plan view of the nozzle and manifold portion of the de-paraffinizing module of FIG. 3.
Figure 3:
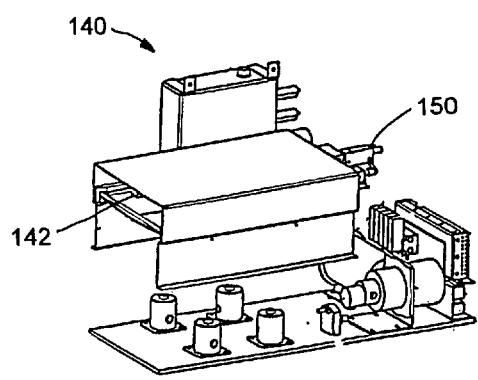
FIG. 3 is an exploded perspective view of a de-paraffinizing module portion of a first embodiment of the present invention.

Referring in particular to FIGS. 3 and 3A, de-paraffinizing station 140 comprises a modular compartment and includes one or a plurality of wash dispense nozzles 142 directed downward at an angle to specimen slides. Preferably, de-paraffinizing station 140 comprises two banks 144A,B often nozzles 142 each supplied via common manifolds 146A,B with a suitable de-paraffinizing fluid from a de-paraffinizing fluid supply 32 which, in a preferred embodiment of the invention, comprises heated water and detergent. Alternatively, a pair of nozzles 142 may be mounted on a moveable fixture, and advanced from slide pair to slide pair.

Various de-paraffinizing agents may be used, and preferably comprise aqueous-based fluid such as disclosed in co-pending U.S. patent application Ser. No. 09/721,096 filed Nov. 22, 2000 and U.S. Pat. No. 6,544,798, issued Apr. 8, 2003, including deionized water, citrate buffer (pH 6.0-8.0), tris-HCl buffer (pH 6-10), phosphate buffer (pH 6.0-8.0), FSC buffer, APK wash™, acidic buffers or solutions (pH 1-6.9) basic buffers or solutions (pH 7.1-14), which are given as exemplary. If desired, the aqueous-based fluid may also contain one or more ionic or non-ionic surfactants such as Triton X-100™, Tween™, Brij, Saponin and Sodium Dodecylsulfate. Typically, the de-paraffinizing fluid is heated. For example, if the embedding medium is paraffin, which has a melting point between 50-57 degrees C., the fluid should be heated to a temperature greater than the melting point of paraffin, e.g. between 60-70 degrees C. Typically, the fluid is heated in the fluid supply.

Figure 5:
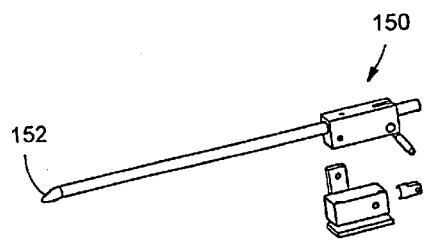
FIG. 5 is a perspective view showing details of the de-paraffinizing fluid recovery system of a first embodiment of the present invention.
Figure 6:
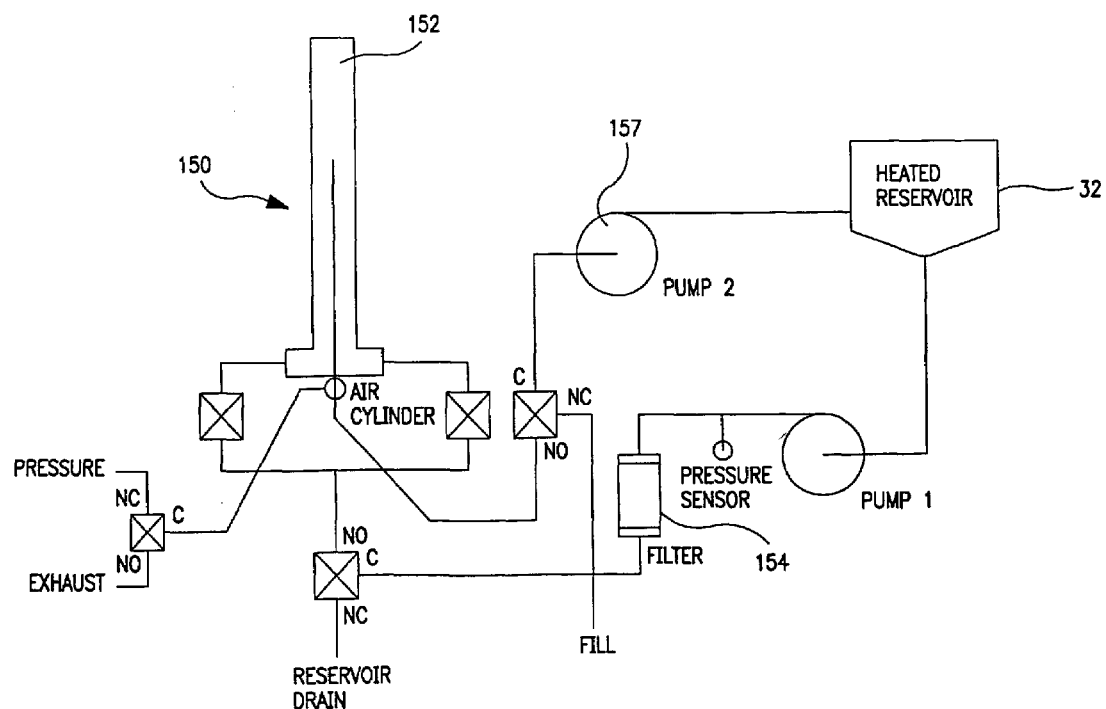
FIG. 6 is a schematic plumbing diagram of the de-paraffinizing fluid system of a first embodiment of the present invention.

Referring also to FIGS. 5 and 6, the de-paraffinizing station 140 also includes a fluid aspirating probe 150 arranged for pivotal movement of its distal end 152 to central location 104 of a tray 80 when the latter is positioned in de-paraffinizing station 140. Probe 150 comprises a hollow tube connected via tubing (not shown) and an aspirating pump 157 to a de-paraffinizing agent separator (not shown) wherein the de-paraffinizing fluid, returned to the fluid supply 32 where it is heated by a heater, as necessary, filtered, in a filter 154 to remove cells as may have been dislodged during the de-paraffinizing process, and reused. If desired, accumulated paraffin may be removed, for example, by skimming. Probe 150 should have sufficient freedom of movement between a deployed position wherein the probe is located adjacent the central location 104 of the tray, and a parked position above the tray and slide so as to not interfere with movement of the tray and slides into and out of the de-paraffinizing station 140.

A feature and advantage of the present invention, particularly as compared to conventional bath-type de-paraffinizing stations is that the potential of cross-contamination between slides, e.g. from the possibility of cell carryover from one slide to another is eliminated since the specimen slides are subjected only to fresh-filtered de-paraffinizing fluid, and the horizontal, co-planar, spaced orientation of the specimen slides in the tray prevents possible cross-contamination by cell carryover between slides during the paraffinizing process. Moreover, the de-paraffinizing process is made more efficient by the use of heated de-paraffinizing agent.

Figure 7:
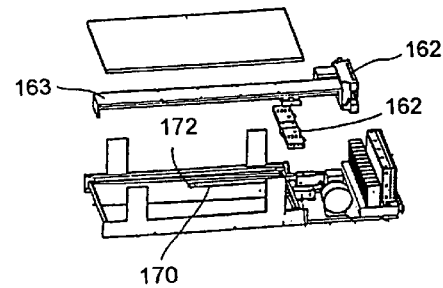
FIG. 7 is a view, similar to FIG. 3, of a stain applicator station module of the present invention.

Referring in particular to FIG. 7, the staining station 160 comprises a modular compartment and includes two or more stain-dispensing and rinsing nozzles 162. In a preferred embodiment of the invention, the staining station comprises a pair of stain-dispensing nozzles 162, which are stepped along a shaft 163 by a screw drive 165 and linear motor (not shown) from pairs of specimen slide to specimen slide. Stain dispensing nozzles 162 are selectively connected via valves and conduits and positive pressure pumps (not shown) to stain reservoirs 168A, B, C and D, and alternatively the nozzles are selectively connected to a rinse liquid source, normally DI water optionally including surfactant.

A fluid aspirating nozzle 170, similar to fluid aspirating nozzle 150, is provided in staining station 160 and is pivotally movable between a working position in which the distal end 172 of the nozzle is adjacent central location 104 of a tray in staining station 160, and a parked position above the tray and slides so as to not interfere with movement of a tray and slide into and out of the staining station 160. Aspirating nozzle 170 is connected through tubing (not shown) and an aspirating pump (not shown) to a waste container 38. As in the case of the de-paraffinizing station, the horizontal, co-planar spaced orientation of the slides in the tray prevents cross-contamination of slides during the staining process.

The cover slipping station 180 which also comprises a modular unit may comprise a fluid coverslip dispenser for applying a conventional fluid coverslipper such as described in U.S. Provisional Patent Application Ser. No. 60/375,925, filed Apr. 26, 2002, entitled "Automated Coverslipper" and incorporated herein by reference.

Figure 8:
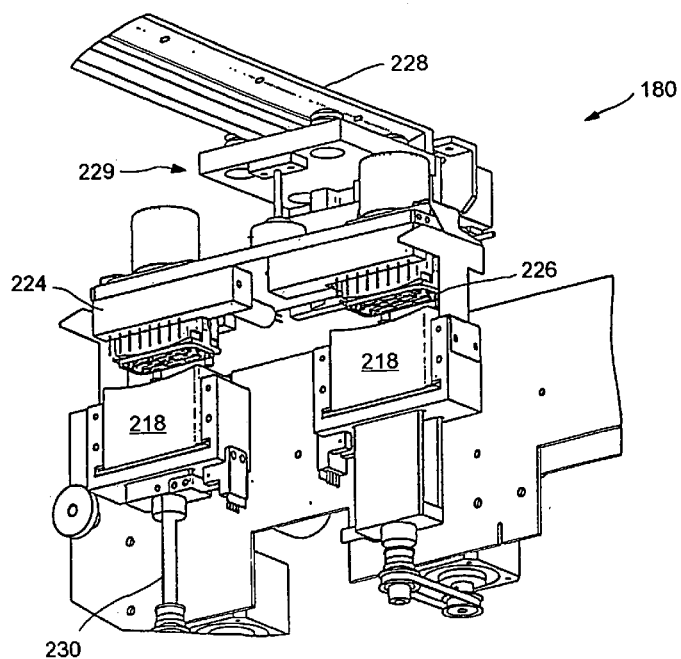
FIG. 8 is a perspective view of the coverslipper module of the present invention.
Figure 8A:
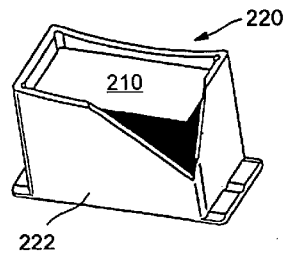
FIG. 8A is a perspective view of a coverslipper cartridge portion of the coverslipper module shown in FIG. 8.

Alternatively, and in a preferred embodiment as illustrated in FIGS. 8 and 8A, the coverslipping station 180 includes a cartridge or magazine 218, having an open dispensing end 220. The magazine 218 defines a substantially rectangular box 222, wherein glass plate coverslips 210 are stacked in a substantially vertical arrangement. A transfer mechanism, generally designated 224, removes the top, or uppermost glass plate coverslips 210 from the box 222, and onto the waiting glass specimen slide 56. In a preferred embodiment, transfer mechanism 224 includes a suction cup 226 suspended from a rail 228 and reciprocally driven along the rail by a linear motor and drive 229. A reciprocally vertically moveable plunger 230 extending through the bottom of box 222 pushes the stack of glass plate coverslips into contact with suction cup 226 wherein the suction cup 226 engages the top glass plate coverslip 210. The plunger 230 is then retracted whereby the stack of glass plate coverslips 210 are separated from the top glass plate coverslip which is retained by the suction cup 226. The suction cup 226 is then advanced along the rail 228 to over a selected slide, and the suction cup prompted to release the glass plate coverslip onto the slide. The suction cup is then returned to above the magazine 218, and the plunger 230 again activated to push the stack of glass plate coverslips 210 into contact with suction cup 226, and the process repeated.

The glass plate coverslips 210 each have a substantially planar top and bottom surface and a substantially rectangular configuration, with a length and a thickness slightly less than the specimen slide 56.

In a particularly preferred embodiment, each of the glass plate coverslips 210 are coated, on their bottom surface, with a dry activatable adhesive. In such case, a fluid dispensing nozzle 232 is carried by drive 228 in advance of the glass plate coverslip 210 for applying an adhesive activating fluid over the surface of the specimen slide. Preferred adhesives include Permount™ (Fisher Scientific, Pittsburgh, Pa.) or ShurMount™ (Triangle Biomedical, Durham, N.C.), which may be activated by a low viscosity fluid such as toluene or xylene. An advantage to employing adhesive coated glass coverslips and low viscosity adhesive activating fluid such as xylene is that air pockets, i.e., between the specimen slides 56 and the glass plate coverslips 210 are largely avoided. U.S. application Ser. No. 09/716,344, filed Nov. 20, 2000 further described the pre-glued coverslip, and is incorporated herein by reference in its entirety.

The slide tray 54 is transported between the aforesaid work stations by means of an X-Y-Z transport and elevator mechanism. Referring in particular to FIGS. 1A, 1B, 9, 10A and 10B, the transport elevator mechanism includes a slide tray support table 60 comprising a generally rectangular frame 62 slidably mounted on an elevator rail 64. Frame 62 is connected, via a bracket 74 to an elevator drive assembly 76 driven by an elevator transmission and drive motor 78. A counterweight 5 is provided to offset the weight of the slide tray and temper acceleration and deceleration forces on the slide tray.

Figure 9:
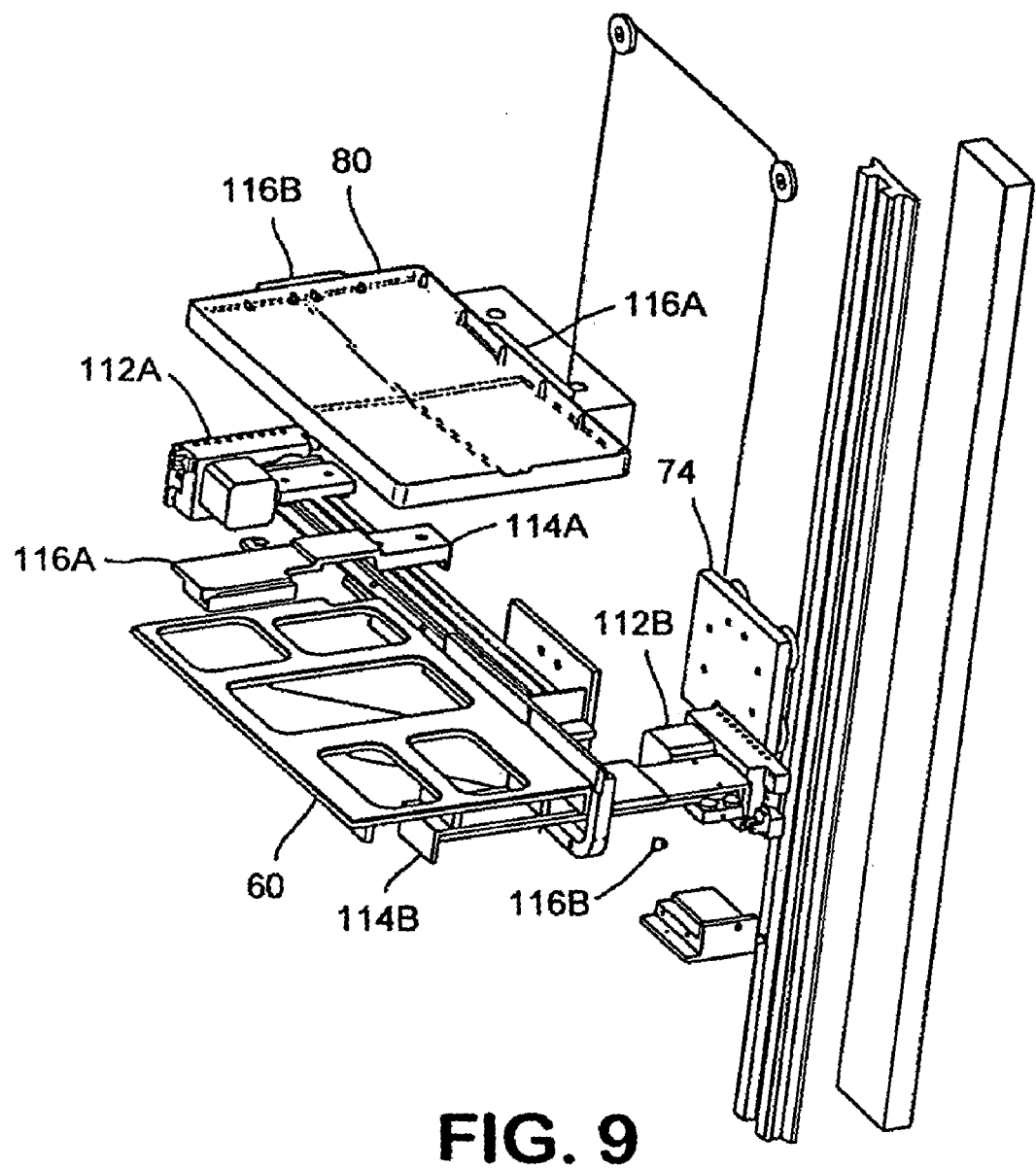
FIG. 9 is an exploded view showing details of the slide tray transport and elevator portion of the present invention.
Figure 10A:
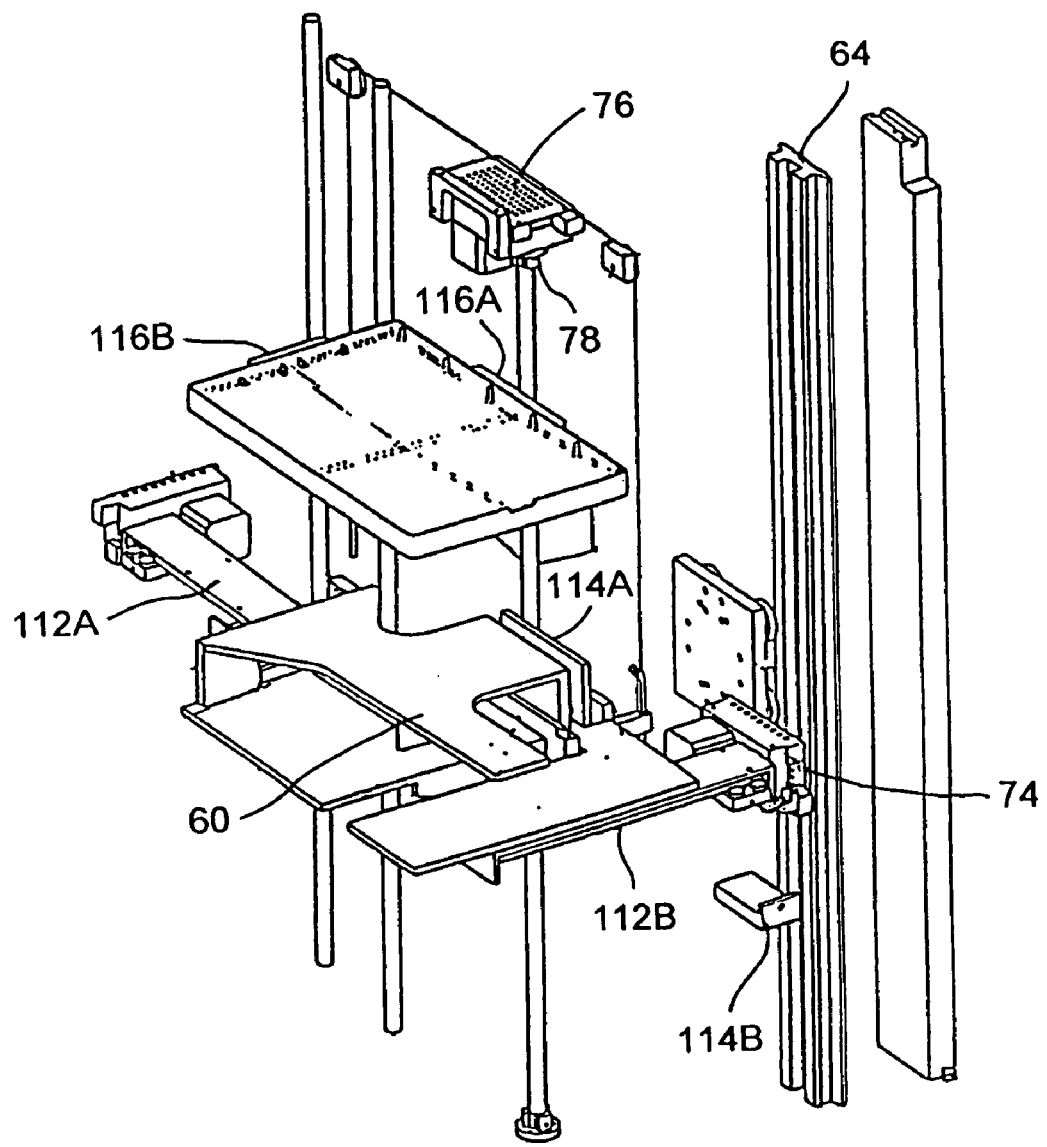
FIGS. 10A and 10B are two different perspective views showing details of the X-Y table of the slide tray transport and elevator portion of the present invention.
Figure 10B:
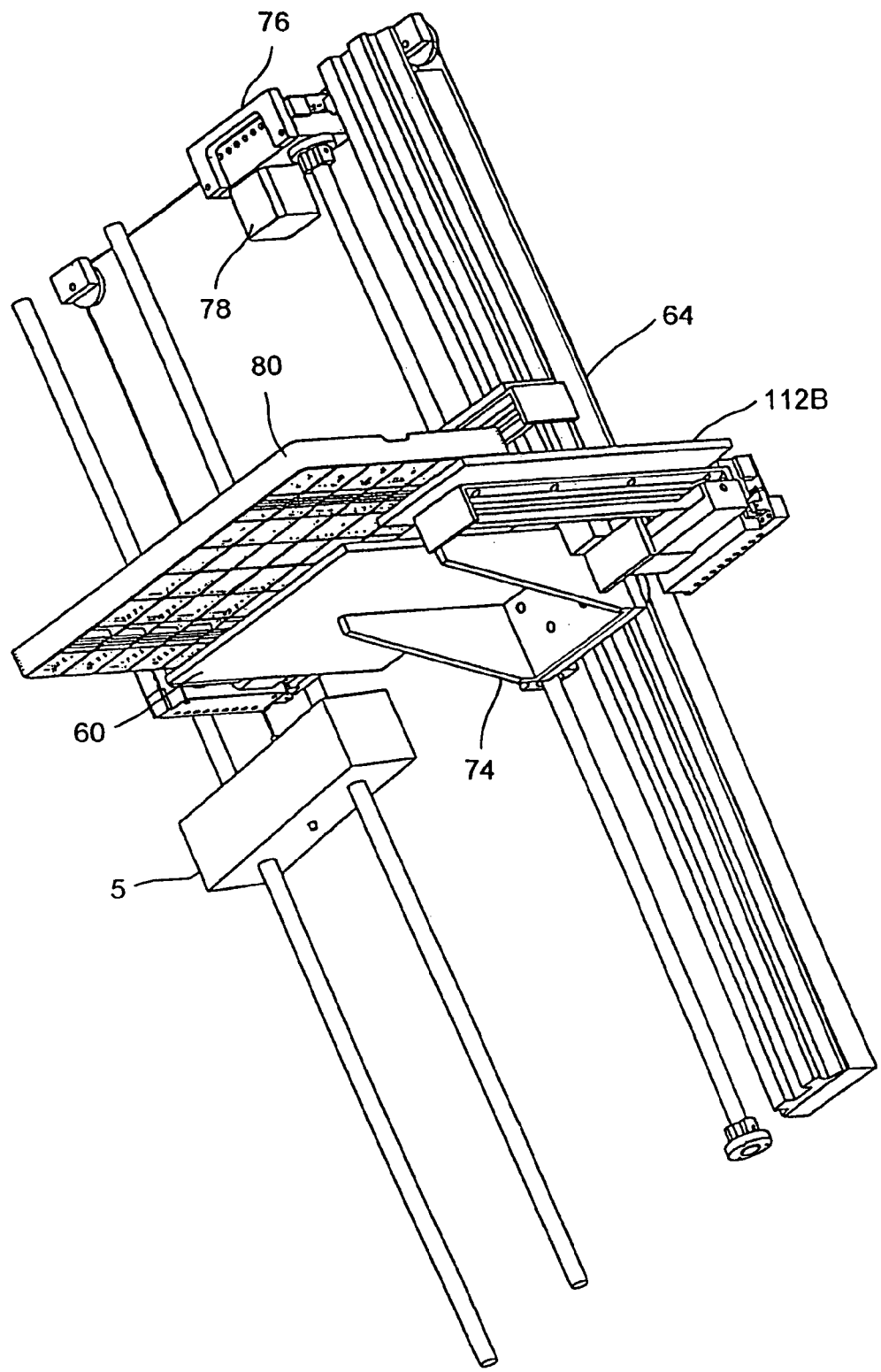

Referring in particular to FIGS. 9, 10A and 10B, the slide support table 60 also includes an X-Y loading/unloading transfer mechanism 110 that includes stepper motor driven drive systems 112A, 112B carrying upwardly extending brackets 114A, 114B for engaging downwardly extending brackets 116A, 116B on a tray 80, for shuttling the tray 80 on and off the transport and elevator mechanism and into and from a selected work station as will be described in detail below.

In order to ensure each tray is appropriately positioned in a work station, the transport/elevator mechanism includes proximity sensors such as optical sensors 118 or microswitch sensors (not shown). Hall-effect sensors may also be used.

Operation of the above-described apparatus will now be provided.

Figure 11:
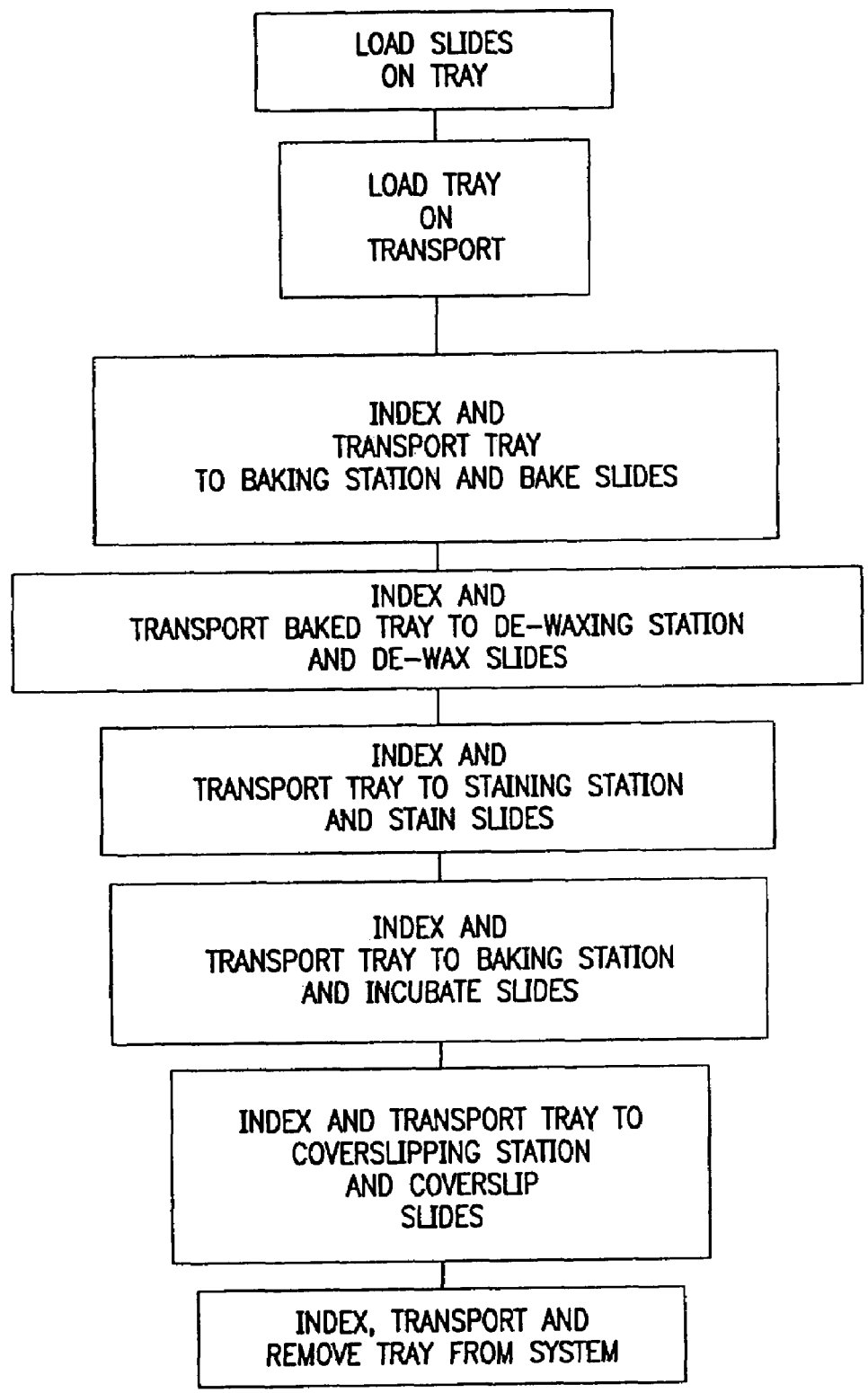
FIG. 11 is a flow diagram illustrating a first embodiment of the present invention.

Referring to FIG. 11, specimen-bearing slides 56 are placed on slide tray 54. The slide tray 54 is loaded into garage 60 through portal 66. The transport and elevator mechanism is indexed to just below the slide tray 54, and the slide tray is advanced into the garage to a position where the downwardly extending bracket 116A carried on the tray 54 is moved past the upwardly extending bracket 114A carried on the transport/elevator mechanism. The transport elevator mechanism is then indexed in a vertical direction to align the floor of the elevator to approximately the level of the bottom of the tray 54, and the tray is drawn onto the transport/elevator by retracting bracket 114A. The transport elevator mechanism is then moved vertically in a "Z" direction to a position adjacent to the baking station 42. The slide tray is then pushed by bracket 114B in an "X" direction into baking station 42, where the tray is deposited. Bracket 114B is withdrawn, the tray carrying the specimen-bearing slides is baked for a predetermined period of time at a predetermined temperature, i.e. to soften the paraffin on the slides. The transport/elevator is then indexed vertically so that the floor of the elevator is slightly below the level of the bottom of tray 54 adjacent to baking station 42, and bracket 114B is advanced to just past bracket 116B on the tray. The transport/elevator is then adjusted vertically upwardly so as to align the floor of the elevator to approximately the level of the bottom of the tray 54 in the baking station 42, and bracket 114B retracted to drag the tray carrying the baked slides out of the baking station 42, and the tray is then transported, as before, by the transport/elevator mechanism to de-waxing or de-paraffinizing station 44, wherein the tray is deposited in station 44, and the slides are sprayed with heated water or de-paraffinizing fluid to remove paraffin. Typically, alternating banks of slides are flooded with de-paraffinizing fluid from nozzles 142 in a timed sequence. The de-paraffinizing fluid collects in the bottom of tray 80, where it is removed by aspirating nozzle 150, filtered through a 1 micron filter and recycled. In order to prevent excess foaming of aspirated de-paraffinizing agent, waste container 34 preferably is vented to the atmosphere.

The aspirating nozzle 150 is retracted, the slide tray 54 carrying the de-paraffinized specimen slides is then removed from the de-paraffinizing station 140, and transported, as before, by the transport/elevator to staining station 160, wherein a selected stain is applied to individual slides. Selected stains include hematoxylin, eosin, or any other chemical stain useful to highlight the morphology of the tissue sample. Excess stain and wash or rinsate is removed from the bottom of the tray by means of an aspirating nozzle, which is lowered into the center of the tray, and routed to waste. Thus, fresh stain is always employed, whereby prior art problems inherent in convention bath type stainers, including cross-contamination of slides, oxidation of stains and/or depletion of stain activity is eliminated.

The aspirating nozzle is retracted, and the stained slides are then removed from staining station 160, and the tray may be transported again to drying/baking station 120 for drying for a controlled period of time at a controlled temperature. Thereafter, the stained slides are withdrawn from baking station 120, and transported, as before, via the transport/elevator system to coverslipping station 180 wherein a glass coverslip is affixed to the top surface of the slides. The transport/elevator system then moves the coverslipped slides to a storage position in garage 60, or the tray may be returned to the portal position wherein the tray is removed.

DETAILED DESCRIPTION OF SECOND EMBODIMENT

Figure 12:
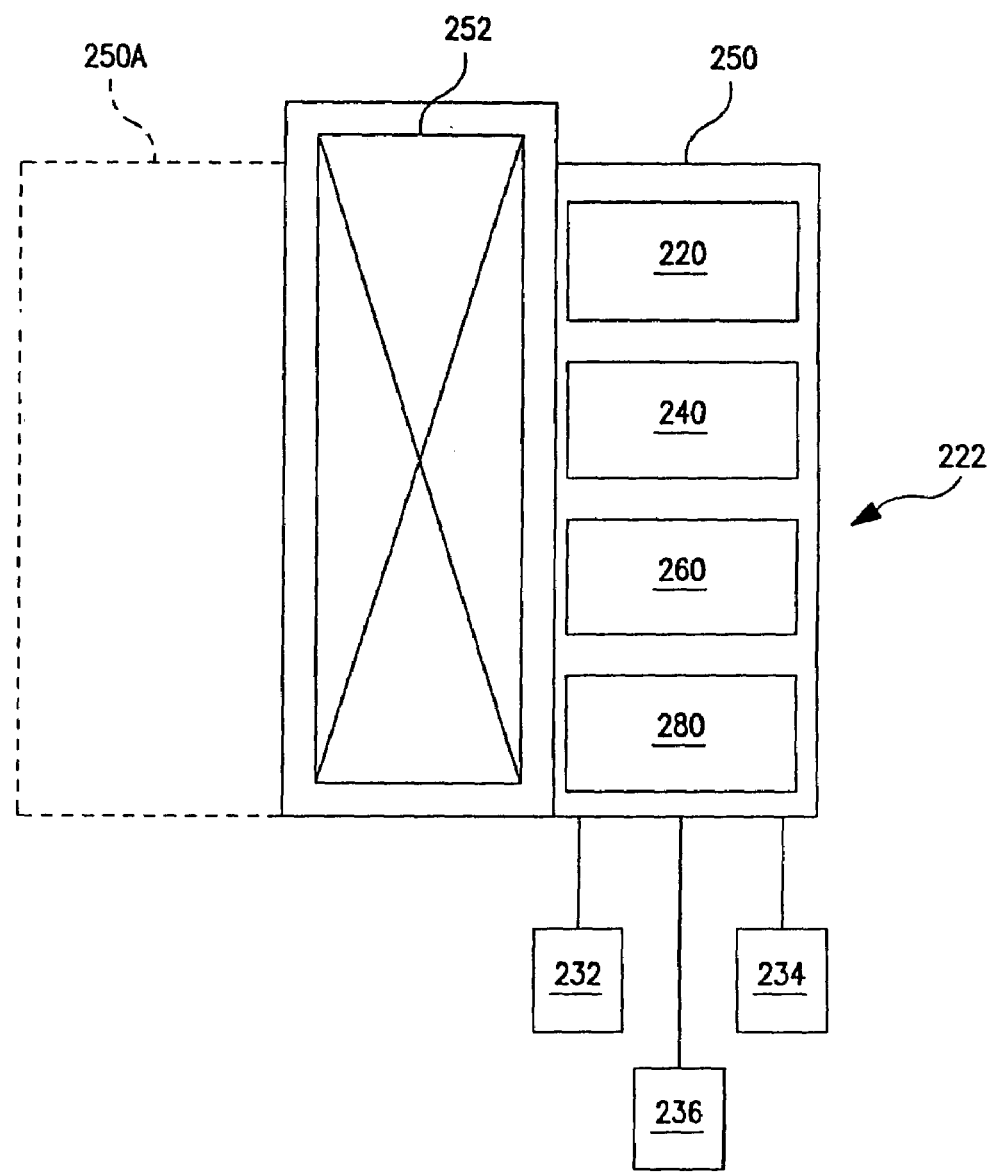
FIG. 12 is a view, similar to FIG. 1, of a second embodiment of an automated high-speed staining apparatus made in accordance with the present invention.

Referring to FIG. 12 of the drawings, the apparatus 220 of the second embodiment of the invention, like the apparatus of the first embodiment, functions as one component or module of a system 222. System 222 also includes bulk fluid containers 232, 234, 236 and related equipment.

As in the case of the first embodiment, apparatus 220 includes a frame supporting a stack of workstations comprising, for example, one or more drying or baking stations or modules, a de-waxing or de-paraffinizing station or module, one or more staining stations or modules 260 and a coverslipping station or module 280 arranged in a tower 250. However, in the second embodiment the baking station and the de-paraffinizing station are combined in a single module 220. A transport and elevator mechanism 252, similar to transport and elevator mechanisms 52 previously discussed, is provided adjacent tower 250 for transporting a slide tray 54 (see FIG. 13) designed to carry a plurality of individual specimen bearing slides 56 from a tray storage station through drying/baking, de-waxing, staining and coverslipping operations.

In the illustrated embodiment, the combined drying/baking and de-paraffinizing station or module 240, the staining station or module 260, and the coverslipping station or module 280 are vertically arranged in tower 250 and controlled by a computer.

Figure 13:
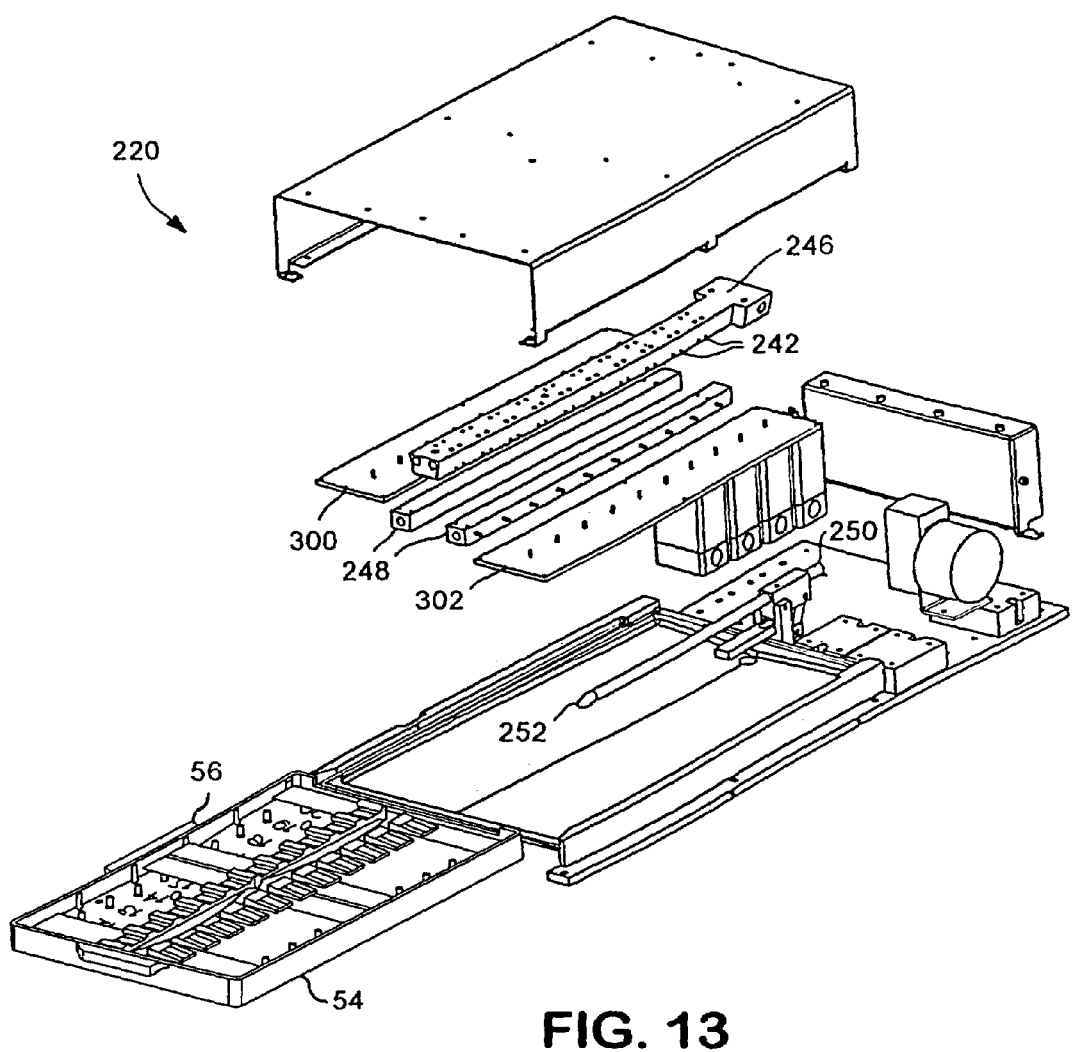
FIG. 13 is an exploded view of a combination baking and de-paraffinizing module portion of the second embodiment of the present invention.

Referring to FIG. 13, the combined drying/baking and de-waxing/de-paraffinizing station 220 comprises a thermally-insulated compartment into which is supplied controlled heat for drying specimen slides. Station 220 preferably comprises a modular unit and includes a pair of radiant heater panels 300, 302, arranged to direct radiant heat onto the surfaces of the specimen slides. Heating the slides serves to dry the slides, soften paraffin on the slides, and heat de-paraffinizing fluid applied to the slides, as will be described in detail below. Station 220 also includes one or a plurality of de-paraffinizing fluid dispense nozzles 242 directed downward at an angle to specimen slides. Preferably, de-paraffinizing station 240 comprises two banks of ten nozzles 242, each supplied via a common manifold 246, with a suitable de-paraffinizing fluid from a de-paraffinizing fluid supply 232 (FIG. 12). Alternatively, a pair of nozzles may be mounted on a moveable fixture, and advanced from slide pair to slide pair.

Various de-paraffinizing agents may be used, and preferably comprise concentrated solutions of aqueous-based fluids such as Collaterge™ (Colonial Chemical, S. Pittsburg, Tenn.). Collaterge may be used as an effective de-paraffinizing agent over a wide range of concentrations, but preferably is used in a concentration of from about 3-30 volume percent. If desired, the concentrated aqueous-based solution may also contain one or more ionic or non-ionic surfactants such as Triton X-100™, Tween™, Brij, Saponin and Sodium Dodecylsulfate. In order to facilitate removal of the embedding medium, i.e., wax, the slides and the de-paraffinizing fluid should be heated. For example, if the embedding medium is paraffin, which has a melting point between 50-57 degrees C., the slides should be baked or pre-heated to a temperature of about 85 degrees C. A feature and advantage of the second embodiment of the invention is that pre-heating of the slides to sufficient temperature eliminates the need to separately pre-heat the de-paraffinizing fluid. Pre-heating the slides, i.e., to soften the paraffin, improves the efficiency of the de-paraffinizing step. Depending on ambient conditions and the amount and type of wax, it may be sufficient to apply the de-paraffinizing fluid to the pre-heated slides, let the fluid work for a few seconds or minutes, and then wash the fluid and wax from the slides using, e.g., deionized water from water nozzles 248. If necessary, the de-paraffinizing fluid covered slides may be baked, e.g., for several minutes, e.g., about 5 minutes, before being washed. Thus, the de-paraffinizing process is enhanced. Moreover, less de-paraffinizing fluid is required, and it is not necessary to filter and recycle de-paraffinizing fluid. Rather, the spent de-paraffinizing fluid may be passed directly to drain, or filtered, and then passed to drain.

Station 240 also includes a fluid aspirating probe 250 similar to 150 in the first embodiment, and arranged for pivotal movement of its distal end 252 to a central location of a tray when the latter is positioned in station 240. Probe 250 comprises a hollow tube connected via tubing (not shown) and an aspirating pump 257 wherein the spent de-paraffinizing fluid may be filtered in a filter (not shown) to remove cells as may have been dislodged during the de-paraffinizing process, and the fluid passed to waste. Probe 250 should have sufficient freedom of movement between a deployed position wherein the probe is located adjacent the central location of the tray, and a parked position above the tray and slide so as to not interfere with movement of the tray and slides into and out of the station 240.

A feature and advantage of the above-described second embodiment of the present invention, particularly as compared to conventional bath-type de-paraffinizing stations is that the potential of cross-contamination between slides, e.g. from the possibility of cell carryover from one slide to another is eliminated since the specimen slides are subjected only to fresh de-paraffinizing fluid, and the horizontal, co-planar, spaced orientation of the specimen slides in the tray prevents possible cross-contamination by cell carryover between slides during the paraffinizing process. Moreover, the de-paraffinizing process is made more efficient by the pre-heating of the slides and/or by heating the de-paraffinizing agent on the slides.

As in the case of the first embodiment, the second embodiment includes a staining station 260, which is similar in construction and operation to staining station 160 previously described, and a coverslipping station 280, similar to coverslipping station 180 previously described. The staining system in accordance with the second embodiment also includes an X-Y-Z transport and elevator mechanism similar to the X-Y-Z transport and elevator mechanism previously described. Of course, in the case of the second embodiment, the apparatus may have one less station or module, and thus timing and sequencing of movement between the several modules will be different as described below.

Operation of the above-described apparatus in accordance with the second embodiment will now be provided.

Figure 14:
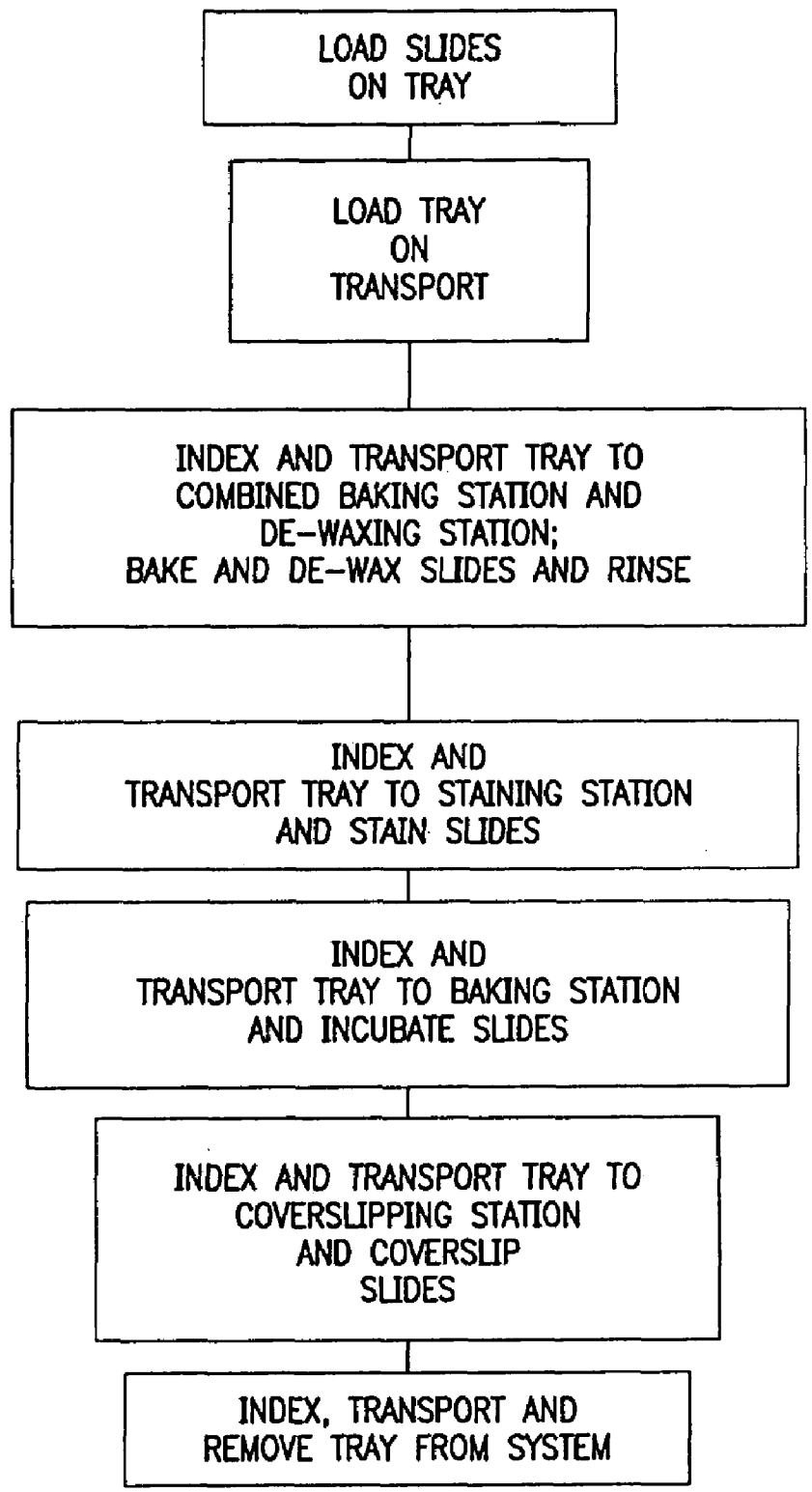
FIG. 14 is a view, similar to FIG. 11, of a flow diagram illustrating the second embodiment of the present invention.

Referring to FIG. 14, specimen-bearing slides are placed on the slide tray, and the slide tray is loaded into the transport and elevator 252. The transport elevator mechanism is then moved vertically in a "Z" direction to a position adjacent to the baking and de-paraffinizing station 242, into which station the tray is deposited. The tray carrying the specimen-bearing slides is baked for a predetermined period of time at a predetermined temperature, i.e. to soften the paraffin on the slides, remove water from the specimen and adhere tissues to the slide. Once sufficiently heated, e.g., to a slide surface temperature of 85 degrees C., the slides are covered with concentrated de-paraffinizing agent, and heated for 5 minutes. If desired, alternating banks of slides may be sprayed with fresh concentrated de-paraffinizing agent from nozzles 242 in a timed sequence. The slides are then rinsed with deionized water to remove the de-paraffinizing agent and the paraffin, and the rinse water, de-paraffinizing agent and paraffin, which collect in the bottom of the slide tray, are removed by aspirating nozzle 250, filtered to remove solids, and the resulting filtrate is passed to waste.

The aspirating nozzle 250 is retracted, the slide tray 54 carrying the de-paraffinized specimen slides is then removed from the baking and de-paraffinizing station 240, and transported, as before, by the transport/elevator to staining station 260, wherein a selected stain is applied to individual slides, as described before.

Stained slides are then removed from staining station 260, and the tray may be transported again to baking station 220 for drying for a controlled period of time at a controlled temperature. Thereafter, the stained slides are withdrawn from baking station 220, and transported, as before, via the transport/elevator system to coverslipping station 280 wherein a glass coverslip is affixed to the top surface of the slides. Coverslipped slides may then be sent to the heating/drying station to accelerate curing. The transport/elevator system then moves the coverslipped slides to storage, or the tray may be removed from the system.

Sequencing and Scheduling

Software for operating the system is referred to as the "Run Tine Executive." One of the responsibilities of the Run Time Executive ("RTE") application is to sequence and schedule the operations performed by the various functional workstations on each tray of microscope slides. The system can handle 25 of these trays at one time with each tray requiring the operations performed by one or more workstation and perhaps multiple visits to the same workstation. Trays are moved within the instrument by a single elevator and a shuttle table. Together, this elevator and table combination can move a tray in the XYZ directions as needed. The instrument also contains a "parking garage" where trays can be placed while they are waiting for a workstation to become available or when all the operations on them are completed. The maximum number of trays, 25, matches the number of parking slots in the garage.

The basis of all actions performed on a tray is a user-selected protocol which, among other items, designates the required workstation operations and the priority of the tray as "STAT" or normal. Using this protocol, the RTE prepares an ordered sequence of workstations to be visited. Since there is only one elevator per table it can be viewed as a single server with multiple jobs to perform. Where the schedule for this problem could be calculated, it is necessary to know that the arrival of trays to the instrument cannot be predicted. Likewise, users can change the priority of a tray at any time. With these factors in mind, the schedule is determined dynamically each time the elevator/table becomes available for work. Elevator/table "work" consists of moving a tray from point A to point B. Thus, after completing a move, the elevator/table is available. At that time, the RTE examines each tray in the system and creates a list of possible moves. The process is as follows:

1. First, determine if a tray can be moved. In order to move a tray, it must be either done in a workstation, parked and ready for the next workstation, parked and ready for removal, or ready to be parked because of an abnormal condition.
2. If the tray can be moved, its next destination must be identified from its planned sequence and checked for availability. A workstation is considered available if it is both empty and operationally ready. If there are more than one of the target workstations available, the workstation that has been waiting the longest is chosen. If the tray's target workstation is not available, then it will be routed to the parking garage. In those instances, the RTE always chooses the empty parking slot closest to the tray's next target station.

Once the list of all possible moves is prepared, the RTE selects the one move to perform. This selection is based on tray priority and in the event of a tie, the time of arrival (TOA) of the tray to the system (i.e. entry time at the portal) determines. The rules governing a tray's priority are as follows:

1. The highest priority is assigned to a tray if it is currently in the slide detect/bar code reading station. This highest priority is assigned because the shuttle table is involved with this station operation and until it has completed and moved the tray to its next station, no other move can be assigned to the elevator/table.
2. The second highest priority is assigned to a tray with a user-designated STAT priority.
3. The third highest priority is assigned to a tray that is either in the portal waiting for entry into the system or is in the garage waiting to be removed from the system. This priority accommodates the instances where a user is standing by waiting for the instrument.
4. The lowest priority is assigned to any tray that does meet the other three criteria. The software mechanics of this selection consists of a record in a dynamic array structure that is made for each tray that can be moved. This record contains tray identification, its assigned priority, and its TOA. The array is sorted by priority and then TOA and the entry at the top of the list is the tray given to the elevator/table to perform.

It is thus seen that the present invention provides an integrated system capable of high throughput staining of biological samples on slides. Amongst the advantages of the present invention are the elimination of conventional dip-and-dunking de-paraffinizing and/or staining baths, which tend to degrade through oxidation and/or contamination by biological cells dislodged during the de-paraffinizing process. Rather, the present invention employs clean, fresh or constantly filtered de-paraffinizing agent, or staining reagent, thus eliminating the possibility of cell carryover from slide to slide. Additionally, reagent utilization is approximately the same on a per slide basis (350 μl) as the dip-and-dunker, a surprising fact. Moreover, the present invention provides for the first time a fully integrated high throughput system for staining slides from the baking step through the coverslipping step, a process that is not performed by any other commercially available system today.

Various changes from the above-described embodiments may be made without departing from the spirit and scope of the invention. For example, the apparatus may include two or more staining station modules, two or more baking station modules, two or more de-paraffinizing station modules and/or two or more combined baking and de-paraffinizing station modules, which may further increase through-put. A particular feature and an advantage of the present invention is that additional station modules may be added vertically without increasing the footprint of the system. Alternatively, two or more additional towers or stacks of work stations 50A, shown in phantom in FIG. 1, may be served by a single transport/elevator system. Other reagents may be utilized on the instrument to perform other tests, including those used for in situ hybridization (typically DNA/RNA probes), or immunohistochemistry (typically antibodies). Yet other changes may be made in the invention without departing from the spirit and scope thereof, the scope of the invention being defined by the appended claims to be interpreted in light of the foregoing specification.

The invention claimed is:

1. A de-waxing or de-paraffinizing station for processing specimen slides, and comprising, a reservoir containing an aqueous-based de-waxing or de-paraffinizing fluid; a heater for heating said aqueous-based fluid; a sprayer for spraying said heated aqueous-based fluid onto said slides; a collector for collecting and returning the aqueous-based fluid to the reservoir; and a filter for filtering the aqueous-based fluid for reuse.

2. A de-waxing or de-paraffinizing station as claimed in claim 1, wherein said filter is located between said collector and said reservoir.

3. A de-waxing or de-paraffinizing station as claimed in claim 1, and further comprising a tray for holding a plurality of specimen slides, spaced from one another, in a substantially horizontal orientation.

4. A de-waxing or de-paraffinizing station as claimed in claim 1, and further comprising a plurality of spray nozzles for spraying said de-waxing or de-paraffinizing fluid onto said slides.

5. A de-waxing or de-paraffinizing station as claimed in claim 3, wherein said tray has a sloped bottom wall, and further including an aspirator for drawing spent de-waxing or de-paraffinizing fluid from adjacent a low point of said sloped bottom wall.

6. A de-waxing or de-paraffinizing station as claimed in claim 3, wherein said tray includes a rack for holding said plurality of slides, spaced from one another, above the bottom wall of the tray.

7. A de-waxing or de-paraffinizing station as claimed in claim 6, wherein said rack includes a plurality of supports that limit axial, lateral and vertical movement of slides in the tray.

8. A de-waxing or de-paraffinizing station as claimed in claim 6, wherein said rack is adapted to hold a plurality of slides in spaced-apart rows.

9. A method of automatically preparing a tissue sample on a microscope slide for pathological analysis, comprising:
   baking the tissue sample onto the slide by having the instrument apply heat to the tissue sufficient to adhere it to the slide;
   deparaffinizing the tissue sample by contacting it with deparaffinizing fluid at a temperature above the melting point of the paraffin, and subsequently rinsing the liquefied paraffin away;
   staining the tissue sample by contacting it with a staining reagent; and
   coverslipping the slide.

10. The method of claim 9, wherein said slide is coverslipped by contacting the stained tissue sample on the slide with a pre-glued coverslip and an adhesive activating fluid.

11. The method of claim 9 wherein said deparaffinizing fluid comprises water and a surfactant.

12. The method of claim 9 wherein said staining reagent comprises hematoxylin and eosin.

13. The method of claim 9, wherein said staining reagent comprises a chemical stain to highlight morphology of the tissue sample.

14. The method of claim 9, wherein said deparaffinizing step further comprises pre-heating the slide to soften an embedding medium.

15. The method of claim 9, wherein a plurality of slides is held in a tray in a substantially horizontal position in the same plane.

16. The method of claim 9, wherein said baking and/or said deparaffinizing step comprises directing radiant heat onto the surface of the slide.

17. The method of claim 9, wherein said baking step comprises drying the slide.

18. The method of claim 9, wherein said baking step comprises softening paraffin on the slide.

19. The method of claim 9, wherein said deparaffinizing step comprises heating said de-paraffinizing fluid applied to said slide.

20. The method of claim 9, wherein staining comprises employing fresh stain.

21. The method of claim 9, wherein baking comprises directing a flow of heated air across the slide.

22. The method of claim 9, further comprising transporting a tray holding a plurality of slides between a plurality of workstations.

23. The method of claim 22, wherein said plurality of workstations is arranged in one or more towers.

24. The method of claim 9, wherein said de-paraffinizing step comprises advancing a pair of nozzles mounted on a moveable fixture from slide pair to slide pair of a plurality of slides arranged in a tray in a horizontal grid two slides wide.

25. The method of claim 9, wherein said deparaffinizing step includes heating said de-paraffinizing fluid in a fluid supply.

26. The method of claim 9 further comprising filtering and reusing said deparaffinizing fluid.

27. The method of claim 9 further comprising moving the slide to a heating/drying station after said coverslipping step to accelerate curing.

28. The method of claim 15, further comprising placing said tray in a parking garage.

29. An automated slide processing apparatus comprising:
   a tray holding a plurality of slides in substantially horizontal and co-planar, spaced positions;
   a plurality of work stations arranged vertically in a stack, at least one of said workstations comprising a de-waxing or de-paraffinizing station, said de-waxing or de-paraffinizing station including a plurality of fluid dispensing nozzles arranged to supply a de-waxing or deparaffinizing fluid onto said slides and a filter and recirculator for filtering and recirculating said de-waxing or de-paraffinizing fluid; and
   a transport/elevator for transporting said fray between said work stations and for moving said tray into and out of said workstations.

30. A combined baking or drying and de-waxing or de-paraffinizing station for processing specimen slides, comprising a radiant beater for heating said slides; a sprayer for spraying de-waxing or de-paraffinizing fluid from a reservoir onto said heated slides; a tray for holding a plurality of specimen slides spaced from one another in a substantially horizontal orientation, wherein said tray has a sloped bottom wall; and an aspirator for drawing spent de-waxing or de-paraffinizing fluid from adjacent a low point of said sloped bottom wall.

31. A combined baking or drying and de-waxing or de-paraffinizing station for processing specimen slides, comprising a radiant heater for heating said slides; a sprayer for spraying de-waxing or de-paraffinizing fluid from a reservoir onto said heated slides; and a tray for holding a plurality of specimen slides spaced from one another in a substantially horizontal orientation, wherein said tray includes a rack for holding said plurality of slides, spaced from one another, above the bottom wall of the tray.

32. A combined baking or drying and de-waxing or de-paraffinizing station as claimed in claim 31, wherein said rack includes a plurality of supports that limit axial, lateral and vertical movement of slides in the tray.

33. A combined baking or drying and de-waxing or de-paraffinizing station as claimed in claim 31, wherein said rack is adapted to hold a plurality of slides in spaced-apart rows.

* * * * *